United States Patent
Iizuka et al.

(10) Patent No.: US 9,643,969 B2
(45) Date of Patent: May 9, 2017

(54) (AZA)INDOLIZINE DERIVATIVE AND PHARMACEUTICAL USE THEREOF

(75) Inventors: Masato Iizuka, Matsumoto (JP); Kazuo Shimizu, Azumino (JP)

(73) Assignee: KISSEI PHARMACEUTICAL CO., LTD., Nagano (JP)

(*) Notice: Subject to any disclaimer, the term of this patent is extended or adjusted under 35 U.S.C. 154(b) by 406 days.

(21) Appl. No.: 13/824,147

(22) PCT Filed: Sep. 28, 2011

(86) PCT No.: PCT/JP2011/072201
§ 371 (c)(1),
(2), (4) Date: May 6, 2013

(87) PCT Pub. No.: WO2012/043638
PCT Pub. Date: Apr. 5, 2012

(65) Prior Publication Data
US 2013/0217878 A1    Aug. 22, 2013

(30) Foreign Application Priority Data
Sep. 29, 2010 (JP) ................. 2010-219600

(51) Int. Cl.
C07D 487/04 (2006.01)
C07D 471/04 (2006.01)
(52) U.S. Cl.
CPC ......... C07D 487/04 (2013.01); C07D 471/04 (2013.01)
(58) Field of Classification Search
CPC .................................................. C07D 471/04
USPC ......... 514/248, 299, 300; 544/235; 546/112, 546/113
See application file for complete search history.

(56) References Cited

U.S. PATENT DOCUMENTS

| | | | |
|---|---|---|---|
| 4,400,387 A | 8/1983 | Rosseels et al. | |
| 8,431,695 B2 | 4/2013 | O'Connor et al. | |
| 2009/0306396 A1 | 12/2009 | Toyoshima et al. | |
| 2010/0056521 A1 | 3/2010 | Shimizu et al. | |
| 2012/0015972 A1* | 1/2012 | Shimizu ............ | C07D 471/04 514/294 |

FOREIGN PATENT DOCUMENTS

| | | |
|---|---|---|
| JP | 56-18979 A | 2/1981 |
| WO | 2007/043400 A1 | 4/2007 |
| WO | 2007/043401 A1 | 4/2007 |
| WO | 2008/126898 A1 | 10/2008 |
| WO | 2008/126901 A1 | 10/2008 |
| WO | 2010/113942 A1 | 10/2010 |

OTHER PUBLICATIONS

Wolff et al (1997).*
Banker et al. (1997).*
Vippagunta et al (2001).*
International Search Report of PCT/JP2011/072201, date of mailing date Dec. 13, 2011.
Written Opinion of PCT/JP2011/072201, date of mailing date Dec. 13, 2011.
International Preliminary Report on Patentability (Form PCT/IB/373) of International Application No. PCT/JP2011/072201 dated Apr. 2, 2013, with Form PCT/ISA/237.

* cited by examiner

Primary Examiner — Paul V Ward
(74) Attorney, Agent, or Firm — Westerman, Hattori, Daniels & Adrian, LLP

(57) ABSTRACT

(Aza)indolizine derivatives represented by Formula (I) having xanthine oxidase inhibitory activities and useful as agents for the prevention or treatment of a disease associated with abnormality of serum uric acid level, prodrugs thereof, salts thereof or the like. In Formula (I), 0 to 2 of $X^1$, $X^2$, $X^3$ and $X^4$ are a nitrogen atom and the others are $CR^1$; one of $T^1$ and $T^2$ represents cyano and the other represents a group represented by Formula (A), with the proviso that when $T^1$ is cyano, at least one of $X^1$ to $X^4$ is a nitrogen atom; $R^1$ independently represents a hydrogen atom, a halogen atom, a hydroxy group, $C_{1-6}$ alkyl, $C_{1-6}$ alkoxy or the like; ring U represents a benzene ring or the like; m represents integral number from 0 to 2; $R^2$ independently represents a fluorine atom, a hydroxy group or the like.

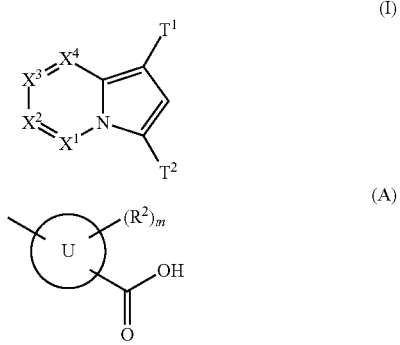

22 Claims, No Drawings

(AZA)INDOLIZINE DERIVATIVE AND PHARMACEUTICAL USE THEREOF

TECHNICAL FIELD

The present invention relates to (aza)indolizine derivatives useful as medicaments.

More particularly, the present invention relates to (aza) indolizine derivatives having xanthine oxidase inhibitory activities and useful as agents for the prevention or treatment of a disease associated with abnormality of serum uric acid level, or prodrugs thereof, or pharmaceutically acceptable salts thereof or the like.

BACKGROUND ART

Uric acid is the final product of purine metabolism in human. In many mammals, unlike human, uric acid is further broken down by urate oxidase (uricase) in the liver into allantoin, which is excreted through the kidney. In human, main pathway of uric acid excretion is the kidney, wherein approximately two thirds of uric acid is excreted in urine. The remaining is excreted in feces. When an excessive production or decreased excretion of uric acid occurs, that causes hyperuricemia. Hyperuricemia is classified into a uric acid overproduction type, a uric acid underexcretion type and a mixed type thereof. This classification of hyperuricemia is clinically important. Aiming for reducing adverse effects of therapeutic agents, therapeutic agents are chosen according to each class (for example, see Non-patent reference 1).

In hyperuricemia with a uric acid overproduction type, urinary excretion of uric acid increases, and when the urinary excretion of uric acid further increases by using of a uricosuric drug, the complication of urinary calculi is possibly developed. Therefore, in principle, allopurinol, a uric acid production inhibitor (or sometimes called a uric acid synthesis inhibitor, hereinafter referred to as "a uric acid production inhibitor"), is used in a uric acid overproduction type.

Uric acid is produced from purine bodies, which are derived from diet and synthesized endogenously, finally by oxidizing xanthine by xanthine oxidase. Allopurinol is developed as a xanthine oxidase inhibitor and an only uric acid production inhibitor used in medical practice. While allopurinol, however, is reported being effective in hyperuricemia and various diseases caused by the same, severe adverse effects such as poisoning syndrome (hypersensitivity angiitis), Stevens-Johnson syndrome, exfoliative dermatitis, aplastic anemia, liver dysfunction and the like have been also reported (for example, see Non-patent reference 2). As one of the causes, it has been pointed out that allopurinol has a nucleic acid-like structure and inhibits a pathway of pyrimidine metabolism (for example, see Non-patent reference 3).

On the other hand, in hyperuricemia with a uric acid underexcretion type, uric acid excretion decreases. It has been reported that when allopurinol, which is metabolized into oxypurinol to be excreted through the kidney by the same mechanism to uric acid, is used, the excretion of oxypurinol also decreases and that increases the incidence of liver disorders (for example, see Non-patent reference 4). Therefore, in principle, uricosuric drugs such as probenecid, benzbromarone and the like are used in a uric acid underexcretion type. These uricosuric drugs, however, also exert adverse effects such as gastrointestinal disorders, urinary calculi or the like. Particularly, benzbromarone is known as possibly causing fulminant hepatitis in the case of idiosyncratic patients (for example, see Non-patent references 5 and 6).

Thus, it is said that both of the existing uric acid production inhibitor and uricosuric drug have usage restrictions in patients or severe adverse effects. Therefore, the development of an easy-to-use agent for the treatment of hyperuricemia or the like has been desired.

Uric acid is eliminated mainly by the kidney, and the urate dynamics in the kidney has been investigated so far in some experiments using brush-border membrane vesicles (BBMV) prepared from the renal cortex (for example, see Non-patent references 7 and 8). It has been known that in human, uric acid is passed through the kidney glomerulus freely, and there are mechanisms of reabsorption and secretion of uric acid in the proximal tubule (for example, see Non-patent reference 9).

In recent years, the gene (SLC22A12) encoding the human kidney urate transporter has been identified (for example, see Non-patent reference 10). The transporter encoded by this gene (urate transporter 1, hereinafter referred to as "URAT1") is a 12-transmembrane type molecule belonging to OAT family. URAT1 mRNA was specifically expressed in the kidney, and localization of URAT1 in apical side of the proximal tubule was observed on the human kidney tissue section. In an experiment using *xenopus oocyte* expression system, uptake of uric acid through URAT1 was shown. Furthermore, it was shown that the uptake of uric acid is transported by exchange with organic anions such as lactic acid, pyrazinecarboxylic acid (PZA), nicotinic acid and the like, and the uric acid uptake through URAT1 is inhibited by uricosuric drugs, probenecid and benzbromarone. Thus, as expected by the experiment using membrane vesicles, it was strongly suggested that URAT1 is a urate/anion exchanger. That is, it was shown that URAT1 is a transporter that plays an important role in uric acid reabsorption in the kidney (for example, see Non-patent reference 10).

In addition, the relation between URAT1 and diseases became clear. Idiopathic renal hypouricemia is a disease wherein uric acid excretion is increased due to abnormal urate dynamics in the kidney and the serum uric acid level becomes low. It is known that the disease is often associated with urinary calculi or acute renal failure after exercise. URAT1 was identified as a causative gene of the renal hypouricemia (for example, see Non-patent reference 10). These things also strongly suggest that URAT1 is responsible for controlling the blood uric acid level.

Therefore, a substance having a URAT1 inhibitory activity is useful as an agent for the treatment and prevention of diseases associated with high serum uric acid levels, that is, hyperuricemia, gouty tophus, gouty arthritis, renal disorder associated with hyperuricemia, urinary calculi or the like.

In the treatment of hyperuricemia, it was reported that a combination of allopurinol of a uric acid production inhibitor and an agent having a uricosuric activity lowered the serum uric acid level more strongly than the single use of allopurinol (for example, see Non-patent references 11 and 12). Therefore, when treatment with a single existing agent can not exert effect enough, a higher therapeutic effect can be expected by a combination use of a uric acid production inhibitor and a uricosuric agent. Furthermore, for hyperuricemia with the uric acid underexcretion type, it is considered that since urinary excretion of uric acid can be decreased by lowering serum uric acid level, the risk of urinary calculi caused by the monotherapy with a uricosuric agent can be reduced. In addition, for hyperuricemia with the mixed type, high therapeutic effect is expected. Thus, an agent having both an inhibitory activity of uric acid production and a uricosuric activity is expected to become an extremely useful agent for the prevention or treatment of hyperuricemia or the like.

As a compound having both xanthine oxidase inhibitory activity and URAT1 inhibitory activity, morin, a natural product, is known (see Non-patent reference 13).

Benzoic acid or a salicylic acid derivatives having xanthine oxidase inhibitory activity are known (see Patent references 1-5). However, in the references, anything is neither described nor suggested about an (aza)indolizine derivative of the present invention.

Patent reference 1: International Publication No. WO 2007/043400 pamphlet
Patent reference 2: International Publication No. WO2007/043401 pamphlet
Patent reference 3: International Publication No. WO2008/126898 pamphlet
Patent reference 4: International Publication No. WO2008/126899 pamphlet
Patent reference 5: International Publication No. WO2008/126901 pamphlet
Non-patent reference 1: Atsuo Taniguchi and 1 person, *Modern Physicians,* 2004, Vol. 24, No. 8, pp. 1309-1312
Non-patent reference 2: Kazuhide Ogino and 2 persons, *Nihon Rinsho* (Japan Clinical), 2003, Vol. 61, Extra edition 1, pp. 197-201
Non-patent reference 3: Hideki Horiuchi and 6 persons, Life Science, 2000, Vol. 66, No. 21, pp. 2051-2070
Non-patent reference 4: Hisashi Yamanaka and 2 persons, *Konyosankessyo to Tsufu* (Hyperuricemia and gout), issued by Medical Review Co., 1994, Vol. 2, No. 1, pp. 103-111
Non-patent reference 5: Robert A Terkeltaub, N. Engl. J. Med., 2003, vol 349, pp. 1647-1655
Non-patent reference 6: Ming-Han H. Lee and 3 persons, Drug. Safety, 2008, Vol. 31, pp. 643-665
Non-patent reference 7: Francoise Roch-Ramel and 2 persons, Am. J. Physiol., 1994, Volume 266 (Renal Fluid Electrolyte Physiol. Volume 35), F797-F805
Non-patent reference 8: Francoise Roch-Ramel and 2 persons, J. Pharmacol. Exp. Ther., 1997, Vol. 280, pp. 839-845
Non-patent reference 9: Gim Gee Teng and 2 persons, Drugs, 2006, Vol. 66, pp. 1547-1563
Non-patent reference 10: Atsushi Enomoto and 18 persons, Nature, 2002, Vol. 417, pp. 447-452
Non-patent reference 11: S Takahashi and 5 persons, Ann. Rheum. Dis., 2003, vol. 62 pp. 572-575
Non-patent reference 12: M. D. Feher and 4 persons, Rheumatology, 2003, Vol. 42, pp. 321-325
Non-patent reference 13: Zhifeng Yu and 2 persons, J. Pharmacol. Exp. Ther., 2006, vol. 316, pp. 169-175

DISCLOSURE OF THE INVENTION

Problem that the Invention Aims to Solve

The present invention is to provide an agent which has an inhibitory activity of uric acid production for the prevention or treatment of a disease associated with abnormal serum uric acid level.

Means to Solve the Problem

The present inventors have studied earnestly to solve the above problem. As a result, it was found that (aza)indolizine derivatives represented by the following formula (I) exert an excellent xanthine oxidase inhibitory activity and extremely lower serum uric acid levels, and therefore, they can be a novel agent for the prevention or treatment of a disease associated with abnormal serum uric acid level, thereby forming the basis of the present invention.

That is, the present invention relates to:

[1] an (aza)indolizine derivative represented by the formula (I):

[Chem. 1]

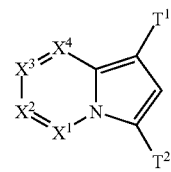

(I)

wherein 0 to 2 of $X^1$, $X^2$, $X^3$ and $X^4$ are a nitrogen atom and the others are $CR^1$;

one of $T^1$ and $T^2$ represents cyano and the other represents a group represented by the formula:

[Chem. 2]

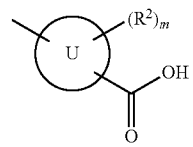

and with the proviso that when $T^1$ is cyano, at least one of $X^1$ to $X^4$ is a nitrogen atom;

$R^1$ independently represents any one of the following (1) to (8):
(1) a hydrogen atom;
(2) a halogen atom;
(3) a hydroxy group;
(4) amino;
(5) carbamoyl;
(6) cyano;
(7) carboxy;
(8) $C_{1-6}$ alkyl, $C_{2-6}$ alkenyl, $C_{2-6}$ alkynyl, $C_{1-6}$ alkoxy, mono(di)$C_{1-6}$ alkylamino, $C_{2-7}$ acyl, $C_{2-7}$ acylamino, mono(di)$C_{1-6}$ alkylcarbamoyl, $C_{1-6}$ alkyl sulfonyl, $C_{1-6}$ alkylsulfonylamino, mono(di)$C_{1-6}$ alkylsulfamoyl, $C_{1-6}$ alkylthio, $C_{3-8}$ cycloalkyl, 3 to 8-membered heterocycloalkyl, $C_{5-8}$ cycloalkenyl, 5 to 8-menbered heterocycloalkenyl, $C_{3-8}$ cycloalkyloxy, $C_{3-8}$ cycloalkylamino, $C_6$ aryl, 5 or 6-membered heteroary, $C_6$ aryloxy, $C_6$ acylamino, $C_6$ arylcarbonyl or $C_6$ arylcarbonylamino each of which may have any group selected from substituent group G;

substituent group G consists of a fluorine atom, a chlorine atom, a hydroxy group, amino, carboxy, carbamoyl, cyano, $C_{1-6}$ alkyl, $C_{1-6}$ alkoxy and mono(di)$C_{1-6}$ alkylamino;

ring U represents a benzene ring or 5 or 6-membered heteroaryl;

m represents an integral number from 0 to 2; and $R^2$ represents a fluorine atom, a hydroxy group, amino, methyl or trifluoromethyl, and when m is 2, two $R^2$ are optionally different from each other, or a prodrug thereof, or a pharmaceutically acceptable salt thereof;

[2] the (aza)indolizine derivative as described in the above [1] wherein the (aza)indolizine derivative represented by the formula (I) is a compound, represented by the following formula (Ia) to (Ii):

[Chem. 3]

(Ia)
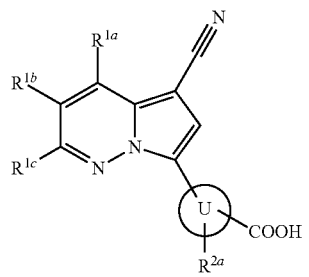

(Ib)
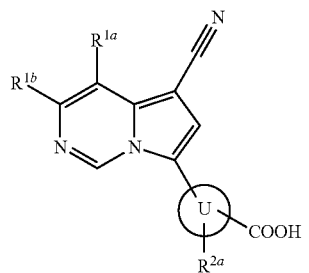

(Ic)
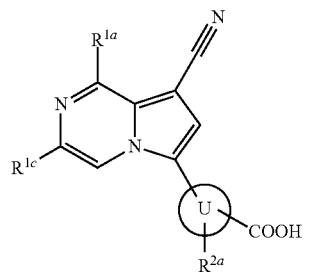

(Id)
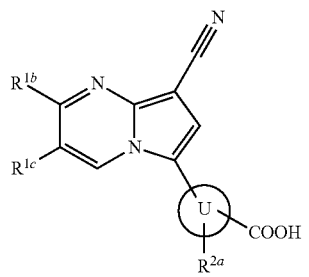

(Ie)
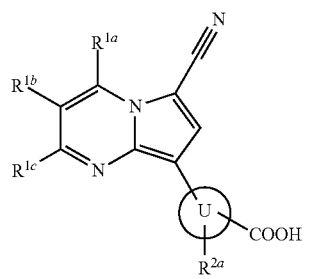

(If)
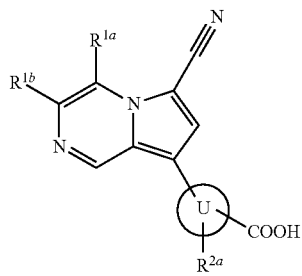

(Ig)
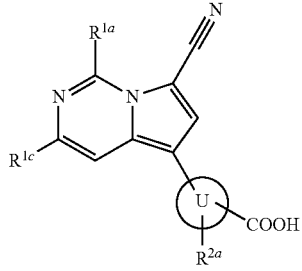

(Ih)
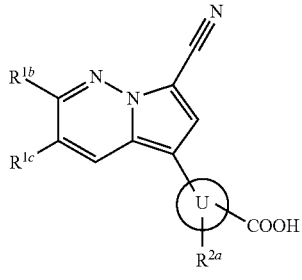

(Ii)
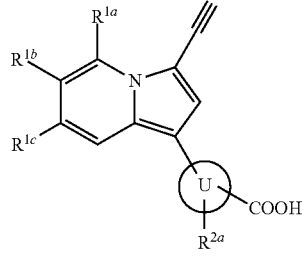

wherein
$R^{1a}$, $R^{1b}$ and $R^{1c}$ independently represent any one of the following (a1) to (a4):
 (a1) a hydrogen atom;
 (a2) a halogen atom;
 (a3) a hydroxy group;
 (a4) $C_{1-6}$ alkyl, $C_{1-6}$ alkoxy, mono(di)$C_{1-6}$ alkylamino, $C_{2-7}$ acyl, $C_{3-8}$ cycloalkyl, 3 to 8-membered heterocycloalkyl, $C_6$ aryl or 5 or 6-membered heteroaryl each of which may have any group selected from substituent group G;

$R^{2a}$ represents a hydrogen atom, a fluorine atom, a hydroxy group or amino; and
ring U and substituent group G have the same meanings as described in the above [1], or a prodrug thereof, or a pharmaceutically acceptable salt thereof;

[3] the (aza)indolizine derivative as described in the above [2], wherein ring U represents a benzene ring, a pyridine ring or a thiazole ring, or a prodrug thereof, or a pharmaceutically acceptable salt thereof;

[4] the (aza)indolizine derivative as described in the above [3], wherein the group represented by the formula:

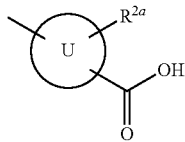

[Chem. 4]

is a group represented by the formula:

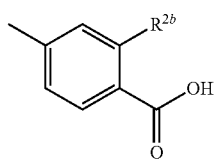

[Chem. 5]

and $R^{2b}$ represents a hydrogen atom or a hydroxy group, or a prodrug thereof, or a pharmaceutically acceptable salt thereof;

[5] the (aza)indolizine derivative as described in the above [3] or [4], wherein $R^{1a}$, $R^{1b}$ and $R^{1c}$ independently represent any one of the following (b 1) to (b4):

(b1) a hydrogen atom;

(b2) a halogen atom;

(b3) a hydroxy group;

(b4) $C_{1-6}$ alkyl, $C_{1-6}$ alkoxy, mono(di) $C_{1-6}$ alkylamino or hydroxy$C_{1-6}$ alkyl each of which may be substituted by a fluorine atom, or a prodrug thereof, or a pharmaceutically acceptable salt thereof;

[6] the (aza)indolizine derivative as described in the above [1], represented by the formula (II):

[Chem. 6]

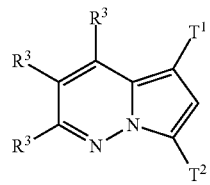

(II)

wherein one of $T^1$ and $T^2$ represents cyano and the other represents a group represented by the formula:

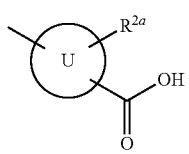

[Chem. 7]

$R^3$ independently represents any one of the following (c1) to (c4):

(c1) a hydrogen atom;

(c2) a halogen atom;

(c3) a hydroxy group;

(c4) $C_{1-6}$ alkyl, $C_{1-6}$ alkoxy, mono(di)$C_{1-6}$ alkylamino, $C_{2-7}$ acyl, $C_{3-8}$ cycloalkyl, 3 to 8-membered heterocycloalkyl, $C_6$ aryl or 5 or 6-membered heteroaryl each of which may have any group selected from substituent group G;

$R^{2a}$ represents a hydrogen atom, a fluorine atom, a hydroxy group or amino; and ring U and substituent group G have the same meanings as described in the above [1], or a prodrug thereof, or a pharmaceutically acceptable salt thereof;

[7] the (aza)indolizine derivative as described in the above [6], wherein $R^3$ independently represents any one of the following (d1) to (d4):

(d1) a hydrogen atom;

(d2) a halogen atom;

(d3) a hydroxy group;

(d4) $C_{1-6}$ alkyl, $C_{1-6}$ alkoxy, mono(di)$C_{1-6}$ alkylamino or hydroxy$C_{1-6}$ alkyl each of which may be substituted by a fluorine atom, or a prodrug thereof, or a pharmaceutically acceptable salt thereof;

[8] the (aza)indolizine derivative as described in the above [7], represented by the formula (IIa):

[Chem. 8]

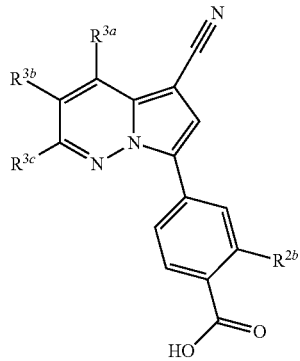

(IIa)

wherein $R^{2b}$ represents a hydrogen atom or a hydroxy group;

$R^{3a}$, $R^{3b}$ and $R^{3c}$ independently represent any one of the following (e1) to (e4):

(e1) a hydrogen atom;

(e2) a halogen atom;

(e3) a hydroxy group;

(e4) $C_{1-6}$ alkyl, $C_{1-6}$ alkoxy, mono(di)$C_{1-6}$alkylamino or hydroxy$C_{1-6}$ alkyl each of which may be substituted by a fluorine atom, or a prodrug thereof, or a pharmaceutically acceptable salt thereof;

[9] the (aza)indolizine derivative as described in the above [7], represented by the formula (IIb):

[Chem. 9]

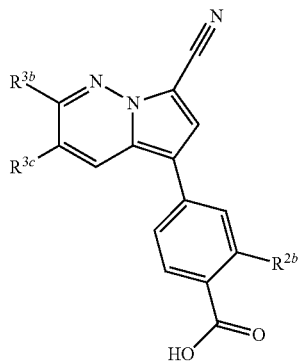

(IIb)

wherein
R$^{2b}$ represents a hydrogen atom or a hydroxy group; and
R$^{3b}$ and R$^{3c}$ independently represent any one of the following (f1) to (f4):
(f1) a hydrogen atom;
(f2) a halogen atom;
(f3) a hydroxy group;
(f4) C$_{1-6}$ alkyl, C$_{1-6}$ alkoxy, mono(di)C$_{1-6}$ alkylamino or hydroxyC$_{1-6}$ alkyl each of which may be substituted by a fluorine atom, or a prodrug thereof, or a pharmaceutically acceptable salt thereof;

[10] the (aza)indolizine derivative as described in the above [8], wherein R$^{2b}$ is a hydroxy group;
R$^{3a}$ is a hydrogen atom, a fluorine atom or a chlorine atom;
R$^{3b}$ is a hydrogen atom, a fluorine atom, methyl, ethyl or methoxy; and
R$^{3c}$ is a hydrogen atom, a fluorine atom, a chlorine atom, methyl or trifluoromethyl, or a prodrug thereof, or a pharmaceutically acceptable salt thereof;

[11] the (aza)indolizine derivative as described in the above [9], wherein R$^{2b}$ is a hydroxy group;
R$^{3b}$ is a hydrogen atom, a fluorine atom, methyl, ethyl or methoxy; and
R$^{3c}$ is a hydrogen atom, a fluorine atom, a chlorine atom, methyl or trifluoromethyl, or a prodrug thereof, or a pharmaceutically acceptable salt thereof;

[12] the (aza)indolizine derivative as described in the above [5], represented by the formula (Ij):

[Chem. 10]

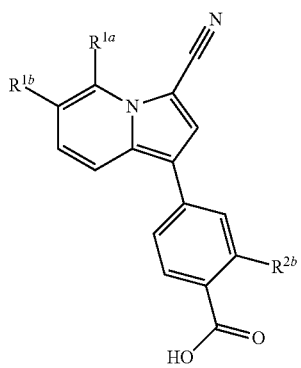

(Ij)

wherein
R$^{2b}$ represents a hydrogen atom or a hydroxy group; and
R$^{1a}$ and R$^{1b}$ have the same meanings as described in the above [5], or a prodrug thereof, or a pharmaceutically acceptable salt thereof;

[13] the (aza)indolizine derivative as described in the above [12], wherein R$^{2b}$ is a hydroxy group;
R$^{1a}$ is a hydrogen atom, a fluorine atom, a chlorine atom or methyl; and
R$^{1b}$ is a hydrogen atom, a fluorine atom, methyl, ethyl or methoxy, or a prodrug thereof, or a pharmaceutically acceptable salt thereof;

[14] a xanthine oxidase inhibitor comprising a compound as described in any one of the above [1] to [13], a prodrug thereof, or a pharmaceutically acceptable salt thereof as an active ingredient;

[15] a pharmaceutical composition comprising a compound as described in any one of the above [1] to [13], a prodrug thereof, or a pharmaceutically acceptable salt thereof as an active ingredient;

[16] the pharmaceutical composition as described in the above [15], which is for the prevention or treatment of a disease selected from the group consisting of hyperuricemia, gouty tophus, gouty arthritis, renal disorder associated with hyperuricemia and urinary calculi;

[17] the pharmaceutical composition as described in the above [16], which is for the prevention or treatment of hyperuricemia;

[18] the pharmaceutical composition as described in the above [15], which is an agent for lowering serum uric acid level;

[19] the pharmaceutical composition as described in the above [15], which is a uric acid production inhibitor; and the like.

As another embodiment, the present invention relates to:
[20] the (aza)indolizine derivative, or a prodrug thereof, or a pharmaceutically acceptable salt thereof as described in the above [1]:
wherein
R$^1$ independently represents any one of the following (1) to (7):
(1) a hydrogen atom;
(2) a halogen atom;
(3) a hydroxy group;
(4) amino;
(5) cyano;
(6) carboxy;
(7) C$_{1-6}$ alkyl, C$_{2-6}$ alkenyl, C$_{2-6}$ alkynyl, C$_{1-6}$ alkoxy, mono(di)C$_{1-6}$ alkylamino, C$_{2-7}$ acyl, C$_{2-7}$ acylamino, mono(di)C$_{1-6}$ alkylcarbamoyl, C$_{1-6}$ alkyl sulfonyl, C$_{1-6}$ alkylsulfonylamino, mono(di)C$_{1-6}$ alkylsulfamoyl, C$_{1-6}$ alkylthio, C$_{3-8}$ cycloalkyl, 3 to 8-membered heterocycloalkyl, C$_{5-8}$ cycloalkenyl, 5 to 8-menbered heterocycloalkenyl, C$_{3-8}$ cycloalkyloxy, C$_{3-8}$ cycloalkylamino, C$_6$ aryl, 5 or 6-membered heteroary, C$_6$ aryloxy, C$_6$ acylamino, C$_6$ arylcarbonyl or C$_6$ arylcarbonylamino each of which may have any group selected from substituent group G;

and the (aza)indolizine derivative, or a prodrug thereof, or a pharmaceutically acceptable salt thereof as described in the above [2] to [19] wherein [1] is replaced with [20], and the like.

As another embodiment, the present invention relates to:
[21] an azaindole derivative, or a prodrug thereof, or a pharmaceutically acceptable salt thereof, represented by the formula (III):

[Chem. 11]

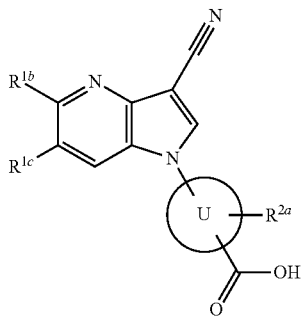

(III)

wherein ring U, $R^{2a}$, $R^{1b}$, and $R^{1c}$ have the same meanings as described in the above [2];

[22] the azaindole derivative, or a prodrug thereof, or a pharmaceutically acceptable salt thereof as described in the above [21], wherein the group represented by the formula:

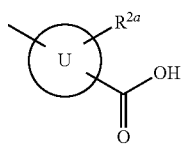

[Chem. 12]

is a group represented by the formula:

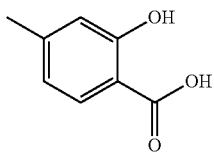

[Chem. 13]

and $R^{1b}$ is a hydrogen atom, a fluorine atom, methyl or methoxy;

$R^{1c}$ is a hydrogen atom, a fluorine atom, a chlorine atom, methyl or trifluoromethyl;

and the azaindole derivative, or a prodrug thereof, or a pharmaceutically acceptable salt thereof as described in the above [14] to [19] wherein [1] to [13] are replaced with [21] or [22], or the like.

In the present invention, each term has the following meaning unless otherwise specified.

The term "5 or 6-membered heteraryl" means a 5 or 6-membered aromatic heterocyclic group having the same or different 1 to 3 hetero atoms selected from an oxygen atom, a sulfur atom and a nitrogen atom in the ring, and thiazolyl, oxazolyl, isothiazolyl, isoxazolyl, pyridyl, pyrimidyl, pyrazinyl, pyridazinyl, pyrrolyl, furanyl, thiophenyl, imidazolyl, pyrazoyl and the like can be illustrated.

The term "halogen atom" means a fluorine atom, a chlorine atom, a bromine atom or an iodine atom.

The term "$C_{1-6}$ alkyl" means a straight-chained or a branched alkyl group having 1 to 6 carbon atoms, for example, methyl, ethyl, propyl, isopropyl, butyl, isobutyl, sec-butyl, tent-butyl and the like can be illustrated.

The term "$C_{1-6}$ alkylene" means a divalent group derived from the above $C_{1-6}$ alkyl.

The term "$C_{2-6}$ alkenyl" means a straight-chained or a branched alkenyl group having 2 to 6 carbon atoms, and vinyl, allyl, 1-propenyl and the like can be illustrated.

The term "$C_{2-6}$ alkynyl" means a straight-chained or a branched alkynyl group having 2 to 6 carbon atoms, and ethynyl, 2-propynyl and the like can be illustrated.

The term "$C_{1-6}$ alkoxy" means a straight-chained or a branched alkoxy group having 1 to 6 carbon atoms, and methoxy, ethoxy, propoxy, isopropoxy and the like can be illustrated.

The term "mono(di)$C_{1-6}$ alkylamino" means an amino group mono- or di-substituted by the above $C_{1-6}$ alkyl.

The term "$C_{2-7}$ acyl" means a group represented by ($C_{1-6}$ alkyl)-C(O)—, and acetyl, propionyl, butyryl, isobutyryl, pivaloyl and the like can be illustrated.

The term "$C_{2-7}$ acylamino" means a group represented by ($C_{1-6}$ alkyl)-C(O)NH—.

The term "mono(di)$C_{1-6}$ alkylcarbamoyl" means a carbamoyl group mono- or di-substituted by the above $C_{1-6}$ alkyl.

The term "$C_{1-6}$ alkylsulfonyl" means a group represented by ($C_{1-6}$ alkyl)-$SO_2$—, and methylsulfonyl, ethylsulfonyl and the like can be illustrated.

The term "$C_{1-6}$ alkylsulfonylamino" means a group represented by ($C_{1-6}$ alkyl)-$SO_2$—NH—, and methylsulfonylamino, ethylsulfonylamino and the like can be illustrated.

The term "mono(di)$C_{1-6}$ alkylsulfamoyl" means a sulfamoyl group mono- or di-substituted by the above $C_{1-6}$ alkyl.

The term "$C_{1-6}$ alkylthio" means a straight-chained or a branched alkylthio group having 1 to 6 carbon atoms, and methylthio, ethykthio and the like can be illustrated.

The term "$C_{3-8}$ cycloalkyl" means a 3 to 8-membered saturated cyclic hydrocarbon group, and cyclopropyl, cyclobutyl, cyclopentyl, cyclohexyl, cycloheptyl, cyclooctyl can be illustrated.

The term "3 to 8-membered heterocycloalkyl" means a 3 to 8-membered heterocycloalkyl group having 1 or 2 hetero atoms selected from an oxygen atom, a sulfur atom and a nitrogen atom in the ring, and aziridino, azetidino, morpholino, 2-morpholinyl, thiomorpholino, 1-pyrrolidinyl, piperidino, 4-piperidinyl, 1-piperazinyl, 1-pyrrolyl, tetrahydrofuryl, tetrahydropyranyl and the like can be illustrated.

The term "$C_{5-8}$ cycloalkenyl" means a 5 to 8-membered cycloalkenyl group, and cyclopropenyl, cyclobutenyl, cyclopentenyl and the like can be illustrated.

The term "5 to 8-membered heterocycloalkenyl" means a 5 to 8-membered heterocycloalkenyl group having 1 or 2 hetero atoms selected from an oxygen atom, a sulfur atom and a nitrogen atom in the ring, and 2,3-dihydrofuryl, 2,5-dihydrofuryl, 3,4-dihydro-2H-pyranyl and the like can be illustrated.

The term "$C_{3-8}$ cycloalkyloxy" means a group represented by ($C_{3-8}$ cycloalkyl)-O— and cyclopropyloxy, cyclobutyloxy, cyclohexyloxy and the like can be illustrated.

The term "$C_{3-8}$ cycloalkylamino" means a group represented by ($C_{3-8}$ cycloalkyl)-NH—.

The term "$C_6$ aryl" means phenyl.

The term "$C_{6-10}$ aryl" means phenyl or naphthyl.

The term "$C_6$ aryloxy" means a group represented by ($C_6$ aryl)-O— and phenyloxy and the like can be illustrated.

The term "$C_6$ arylamino" means a group represented by ($C_6$ aryl)-NH—.

The term "$C_6$ arylcarbonyl" means a group represented by ($C_6$ aryl)-C(O)— and a benzoyl group and the like can be illustrated.

The term "$C_6$ arylcarbonylamino" means a group represented by ($C_6$ aryl)-C(O)NH—.

The term "hydroxy$C_{1-6}$ alkyl" means the above $C_{1-6}$ alkyl mono- or di-substituted by a hydroxy group.

The term "may be substituted by a fluorine atom" means optionally having 1 to 5 fluorine atoms as substituent. And with the proviso that, when the group which may be substituted by a fluorine atom is methyl, methoxy or N-methylamino, it means optionally having 1 to 3 fluorine atoms, or in case of hydroxymethyl, it means optionally having for 2 fluorine atoms.

The term "may have any group selected from substituent group G" means optionally having 1 to 3 same or different groups selected from substituent group G, and having none or 1 substituent is preferred. With the proviso that when the group selected from substituent group G is a fluorine atom, it has the same meaning of the above "may be substituted by a fluorine atom".

The (aza)indolizine derivative represented by the formula (I) of the present invention can be also prepared, for example, by a method described in the following Synthetic methods 1 to 4 or a similar method thereto, a method described in literatures or a similar method thereto or the like. In addition, when a protective group is necessary, operations of introduction and deprotection can be also conducted optionally in combination according to a general method described, for example, "Protective Groups in Organic Synthesis, fourth edition". Each reaction can be also optionally conducted by using a pressure-resistant reaction container. In addition, heating in each reaction can be also optionally conducted under microwave irradiation.

The (aza)indolizine derivative represented by the formula (I) of the present invention can be also prepared by the following Synthetic method 1.

[Synthetic Method 1]

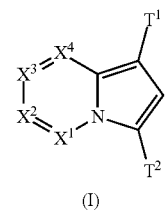

(I)

In the formula, $L^1$ represents a leaving group such as a an iodine atom, a bromine atom, a chlorine atom or the like, $R^a$ represents a hydrogen atom or $C_{1-6}$ alkyl, with the proviso that two $R^a$ are optionally different from each other and optionally bind together to form a ring, and $X^1$ to $X^4$, ring U, $R^2$, m, $T^1$ and $T^2$ have the same meanings as defined above.

Process 1

The (aza)indolizine derivative (I) of the present invention can be also prepared by conducting a coupling reaction of an (aza)indolizine compound (1) or (2) and a boron compound (3) in an inert solvent in the presence of a base and a palladium catalyst. As the inert solvent, benzene, toluene, xylene, diethylether, tetrahydrofuran, 1,4-dioxane, 1,2-dimethoxyethane, dichloromethane, 1,2-dichloroethane, chloroform, N,N-dimethyl formamide, N-methylpyrrolidone, dimethylsulfoxide, water, a mixed solvent thereof and the like can be illustrated. As the base, sodium acetate, potassium acetate, sodium carbonate, potassium carbonate, cesium carbonate, sodium hydroxide, lithium hydroxide, sodium ethoxide, sodium methoxide, potassium fluoride, cesium fluoride, triethylamine, N,N-diisopropyl ethylamine, pyridine, 2,6-lutidine, 1,8-diazabicyclo[5,4,0]-7-undecene and the like can be illustrated. As the palladium catalyst, tetrakis(triphenylphosphine)palladium (0), bis(dibenzylideneacetone)-palladium (0), bis(triphenylphosphine)palladium (II) dichloride, palladium acetate (II), [1,1'-bis(diphenylphosphino)ferrocene] nickel (II) dichloride and the like can be illustrated. The reaction temperature is usually from 0° C. to reflux temperature, and the reaction time is usually from 30 minutes to 7 days, varying based on a used starting material, solvent and reaction temperature or the like.

Among the (aza)indolizine derivatives represented by the formula (I) of the present invention, an (aza)indolizine derivative (IA) wherein $T^1$ is cyano can be also prepared by the following Synthetic method 2.

[Synthetic Method 2]

[Chem. 14]

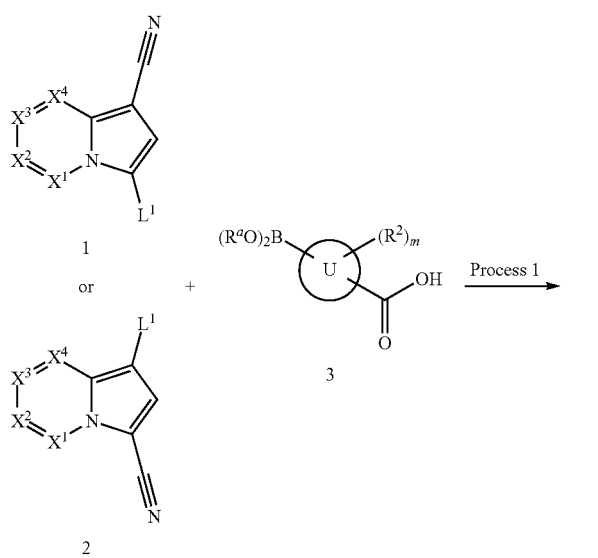

[Chem. 15]

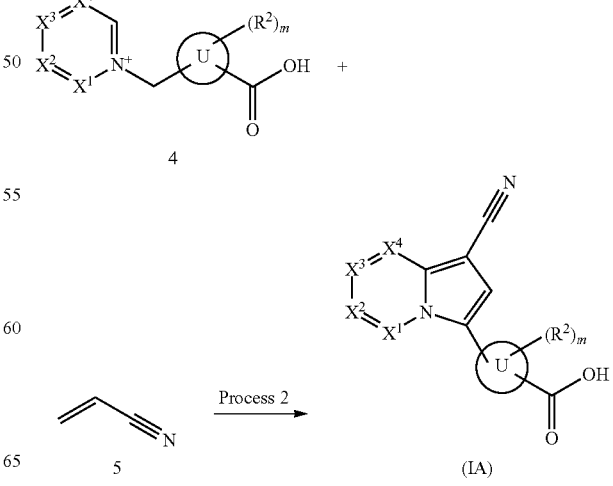

In the formula, $X^1$ to $X^4$, ring U, $R^2$ and m have the same meanings as defined above.

Process 2

The (aza)indolizine derivative (IA) of the present invention can be also prepared by allowing a compound (4) to react with a aceylonitrile (5) in an inert solvent in the presence of a base and manganese dioxide. As the inert solvent, benzene, toluene, xylene, chlorobenzene, diethylether, 1,2-dimethoxyethane, dichloromethane, 1,2-dichloroethane, chloroform, N,N-dimethyl formamide, N-methylpyrrolidone, water, a mixed solvent thereof and the like can be illustrated. As the base, triethylamine, N,N-diisopropylethylamine, pyridine, 2,6-lutidine, 1,8-diazabicyclo[5,4,0]-7-undecene and the like can be illustrated. The reaction temperature is usually at 0° C. to reflux temperature, and the reaction time is usually from 30 minutes to 7 days, varying based on a used starting material, solvent and reaction temperature or the like.

The (aza)indolizine compound (1) used in the above Synthetic method 1 can be also prepared, for example, by the following Synthetic method 3.

[Synthetic Method 3]

[Chem. 16]

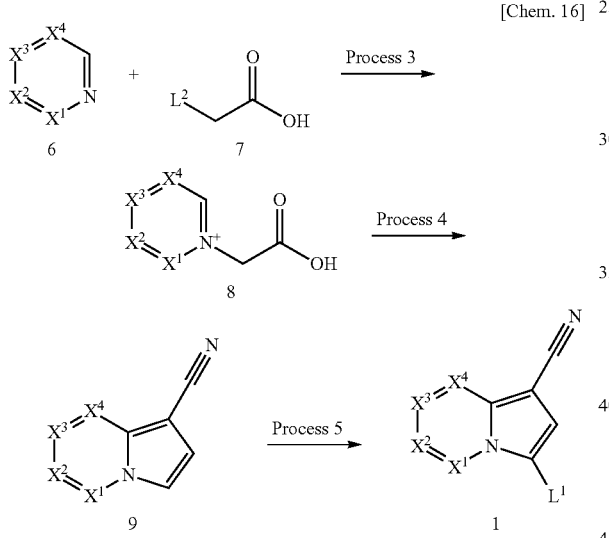

In the formula, $L^2$ represents a leaving group such as a an iodine atom, a bromine atom, a chlorine atom, a mesyloxy group, a tosyloxy group or the like, and $X^1$ to $X^4$ and $L^1$ have the same meanings as defined above.

Process 3

A compound (8) can be also prepared by allowing a heterocyclic compound (6) to react with a carboxylic compound (7) in an inert solvent. As the inert solvent, ethyl acetate, acetone, diethylether, tetrahydrofuran, 1,4-dioxane, 1,2-dimethoxyethane, dichloromethane, 1,2-dichloroethane, chloroform, N,N-dimethylformamide, N-methylpyrrolidone, dimethylsulfoxide, benzene, toluene, xylene, methanol, ethanol, 2-propanol, water, a mixed solvent thereof and the like can be illustrated. The reaction temperature is usually at 0° C. to reflux temperature, and the reaction time is usually from 30 minutes to 7 days, varying based on a used starting material, solvent and reaction temperature or the like.

Process 4

A compound (9) can be also prepared by allowing a compound (8) to react with acrylonitrile in an inert solvent in the presence of a base and manganese dioxide. As the inert solvent, benzene, toluene, chlorobenzene, xylene, diethylether, 1,2-dimethoxyethane, dichloromethane, 1,2-dichloroethane, chloroform, N,N-dimethyl formamide, N-methylpyrrolidone, a mixed solvent thereof and the like can be illustrated. As the base, triethylamine, N,N-diisopropylethylamine, pyridine, 2,6-lutidine, 1,8-diazabicyclo[5,4,0]-7-undecene and the like can be illustrated. The reaction temperature is usually at 0° C. to reflux temperature, and the reaction time is usually from 30 minutes to 7 days, varying based on a used starting material, solvent and reaction temperature or the like.

Process 5

The compound (1) can be also prepared by subjecting a compound (9) to halogenation in an inert solvent in the presence of a halogenating agent. As the inert solvent, dichloromethane, 1,2-dichloroethane, chloroform, carbon tetrachloride, acetic acid, acetonitrile, methanol, N,N-dimethylformamide, a mixed solvent thereof and the like can be illustrated. As the halogenating agent, N-bromosuccinimide, N-chlorosuccinimide, N-iodosuccinimide and the like can be illustrated. The reaction temperature is usually at 0° C. to reflux temperature, and the reaction time is usually from 30 minutes to 7 days, varying based on a used starting material, solvent and reaction temperature or the like.

The (aza)indolizine compound (2) used in the above Synthetic method 1 can be also prepared, for example, by the following Synthetic method 4.

[Synthetic Method 4]

[Chem. 17]

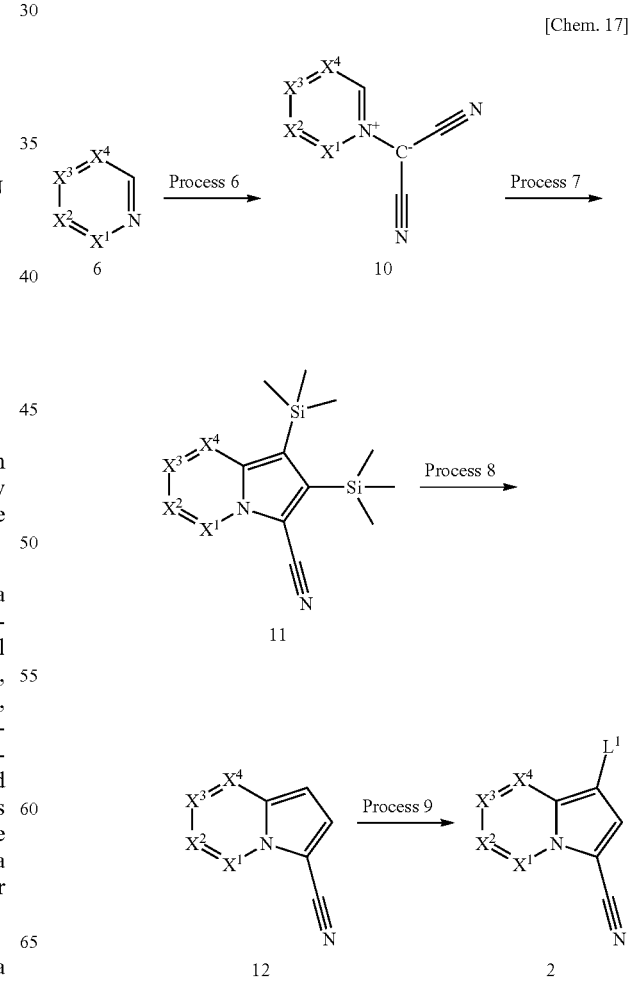

In the formula, $X^1$ to $X^4$ and $L^1$ have the same meanings as defined above.

Process 6

A compound (10) can be also prepared by allowing a heterocyclic compound (6) to react with tetracyanoethylene oxide in an inert solvent. As the inert solvent, ethyl acetate, acetone, diethyl ether, tetrahydrofuran, 1,4-dioxane, 1,2-dimethoxyethane, dichloromethane, 1,2-dichloroethane, chloroform, N,N-dimethylformamide, N-methylpyrrolidone, dimethyl sulfoxide, benzene, toluene, xylene, methanol, ethanol, 2-propanol, a mixed solvent thereof and the like can be illustrated. The reaction temperature is usually at 0° C. to reflux temperature, and the reaction time is usually from 30 minutes to 7 days, varying based on a used starting material, solvent and reaction temperature or the like.

Process 7

A compound (11) can be also prepared by allowing a compound (10) to react with bis(trimethylsilyl) acetylene in an inert solvent. As the inert solvent, benzene, toluene, chlorobenzene, xylene, diethylether, 1,2-dimethoxyethane, dichloromethane, 1,2-dichloroethane, chloroform, N,N-dimethyl formamide, N-methylpyrrolidone, a mixed solvent thereof and the like can be illustrated. The reaction temperature is usually at 0° C. to reflux temperature, and the reaction time is usually from 30 minutes to 7 days, varying based on a used starting material, solvent and reaction temperature or the like.

Process 8

A compound (12) can be also prepared by allowing a compound (11) to react with a fluoride in an inert solvent. As the inert solvent, tetrahydrofuran, 1,4-dioxane, acetone, acetonitrile, N,N-dimethyl formamide, dimethyl sulfoxide, acetic acid, water, a mixed solvent thereof and the like can be illustrated. As the fluoride, tetrabutylammonium fluoride, hydrofluoric acid, cesium fluoride and the like can be illustrated. The reaction temperature is usually at 0° C. to reflux temperature, and the reaction time is usually from 30 minutes to 7 days, varying based on a used starting material, solvent and reaction temperature or the like.

Process 9

A compound (2) can be also prepared by subjecting a compound (12) to halogenation using a halogenating agent in an inert solvent. As the inert solvent, dichloromethane, 1,2-dichloroethane, chloroform, carbon tetrachloride, acetic acid, acetonitrile, methanol, N,N-dimethylformamide, a mixed solvent thereof and the like can be illustrated. As the halogenating agent, N-bromosuccinimide, N-chlorosuccinimide, N-iodosuccinimide and the like can be illustrated. The reaction temperature is usually at 0° C. to reflux temperature, and the reaction time is usually from 30 minutes to 7 days, varying based on a used starting material, solvent and reaction temperature or the like.

As the protective groups used in the above synthetic methods, various protective groups generally used in organic synthesis reaction can be used. For example, as the protective groups of a hydroxy group, in addition to a p-methoxybenzyl group, a benzyl group, a methoxymethyl group, an acetyl group, a pivaloyl group, a benzoyl group, a tert-butyldimethylsilyl group, a tert-butyldiphenylsilyl group, an allyl group and the like, when two hydroxy groups are adjacent, an isopropylidene group, a cyclopentylidene group, a cyclohexylidene group and the like can be illustrated. As the protective groups of a thiol group, a p-methoxybenzyl group, a benzyl group, an acetyl group, a pivaloyl group, a benzoyl group, a benzyloxycarbonyl group and the like can be illustrated. As the protective groups of an amino group, a benzyloxycarbonyl group, a tert-butoxycarbonyl group, a benzyl group, a p-methoxybenzyl group, a trifluoroacetyl group, an acetyl group, a phthaloyl group and the like can be illustrated. As the protective groups of a carboxy group, a $C_{1-6}$ alkyl group, a benzyl group, a tert-butyl-dimethylsilyl group, an allyl group and the like can be illustrated.

The (aza)indolizine derivative represented by the formula (I) of the present invention can be also isolated or purified by conventional isolation techniques such as fractional recrystallization, purification by chromatography, solvent extraction, solid-phase extraction and the like.

The (aza)indolizine derivative represented by the formula (I) of the present invention can be also converted into pharmaceutically acceptable salts thereof in the usual way. As such a salt, an acid additive salt with a mineral acid such as hydrochloric acid, hydrobromic acid, hydroiodic acid, sulfuric acid, nitric acid, phosphoric acid and the like, an acid additive salt with an organic acid such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, benzoic acid, glutamic acid, aspartic acid and the like, a salt with an inorganic base such as a lithium salt, a sodium salt, a potassium salt, a calcium salt, a magnesium salt, a zinc salt, an aluminum salt and the like, an additive salt with an organic base such as N-methyl-D-glucamine, N,N'-dibenzylethylenediamine, 2-aminoethanol, tris(hydroxymethyl) aminomethane, arginine, lysine, piperazine, choline, diethylamine, 4-phenylcyclohexylamine and the like can be illustrated.

Among the (aza)indolizine derivatives represented by the formula (I) of the present invention, in a compound having an unsaturated bond, there are two geometrical isomers, a compound of cis (Z) form and a compound of trans (F) form. In the present invention, either of the compounds can be employed, and a mixture thereof can be also employed.

Among the (aza)indolizine derivatives represented by the formula (I) of the present invention, in a compound having a chiral carbon atom, there are a compound of R configuration and a compound of S configuration for each chiral carbon. In the present invention, either of the optical isomers can be employed, and a mixture of the optical isomers thereof can be also employed.

In the (aza)indolizine derivative represented by the formula (I) of the present invention, there can be some tautomers, and the compounds of the present invention also include these tautomers.

In the present invention, the term "prodrug" means a compound to be converted into a compound represented by the formula (I) within an organism. A prodrug of the compound represented by the formula (I) of the present invention can be prepared by introducing an appropriate group forming a prodrug into any one or more groups selected from a hydroxy group, a carboxy group and other groups which can form a prodrug of the compound represented by the formula (I) using a corresponding reagent to produce a prodrug such as a halide compound or the like in the usual way, and then by suitably isolating and purifying in the usual way as occasion demands. See Gekkan-Yakuji iyakuhin tekiseisiyou no tameno rinsyou yakubutsudoutai (monthly pharmaceutical, clinical pharmacokinetics for the proper use of pharmaceutical products), 2000 March. extra edition, Vol. 42, No. 4, pp. 669-707, and *New Drug Delivery System*, published by CMC Co., Ltd., 2000 Jan. 31., pp. 67-173.

As a group forming a prodrug used in a hydroxy group, for example, $C_{1-6}$ alkyl-CO— such as acetyl, propionyl, butyryl, isobutyryl, pivaloyl and the like; $C_{6-10}$ aryl-CO— such as benzoyl and the like; $C_{1-6}$ alkyl-O—$C_{1-6}$ alkylene-CO—; $C_{1-6}$ alkyl-OCO—$C_{1-6}$ alkylene-CO—; $C_{1-6}$ alkyl-OCO— such as methyloxycarbonyl, ethyloxycarbonyl, propyloxycarbonyl, isopropyloxycarbonyl, tert-butyloxycarbonyl and the like; $C_{1-6}$ alkyl-O—$C_{1-6}$ alkylene-OCO—; $C_{1-6}$ alkyl-COO—$C_{1-6}$ alkylene such as acetyloxymethyl, pivaloyloxymethyl, 1-(acetyloxy)ethyl, 1-(pivaloyloxy)ethyl and the like; $C_{1-6}$ alkyl-OCOO—$C_{1-6}$ alkylene such as methoxycarbonyloxymethyl, 1-(methoxycarbonyloxy)ethyl, ethoxycarbonyloxymethyl, 1-(ethoxycarbonyloxy)ethyl, isopropyloxycarbonyloxymethyl, 1-(isopropyloxycarbonyloxy)ethyl, tert-butyloxycarbonyloxymethyl, 1-(tert-butyloxycarbonyloxy)ethyl and the like; $C_{3-8}$ cycloalkyl-OCOO—$C_{1-6}$ alkylene such as cyclohexyloxycarbonyloxymethyl, 1-(cyclohexyloxycarbonyloxy)ethyl and the like; an ester or an amide with an amino acid such as glycine and the like; and the like can be illustrated.

As a group forming a prodrug used in a carboxy group, for example, $C_{1-6}$ alkyl such as methyl, ethyl, propyl, isopropyl, butyl, tent-butyl and the like; $C_{1-6}$ alkyl-COO—$C_{1-6}$ alkylene such as pivaloyloxymethyl, acetyloxymethyl, 1-(pivaloyloxy)ethyl, 1-(acetyloxy)ethyl and the like; $C_{1-6}$ alkyl-OCOO—$C_{1-6}$ alkylene such as ethyloxycarbonyloxymethyl, 1-(ethyloxycarbonyloxy)ethyl, isopropyloxycarbonyloxymethyl, 1-(isopropyloxycarbonyloxy)ethyl, tert-butyloxycarbonyloxymethyl, 1-(tert-butyloxycarbonyloxy)ethyl and the like; $C_{3-8}$ cycloalkyl-OCOO—$C_{1-6}$ alkylene such as cyclohexyloxycarbonyloxymethyl, 1-(cyclohexyloxycarbonyloxy)ethyl and the like; and the like can be illustrated.

In the present invention, a pharmaceutically acceptable salt also includes a solvate thereof with a pharmaceutically acceptable solvent such as water, ethanol or the like.

The pharmaceutical composition of the present invention is useful for the prevention or treatment of diseases associated with high serum uric acid levels such as hyperuricemia, gouty tophus, gouty arthritis, renal disorder associated with hyperuricemia, urinary calculi or the like, especially for hyperuricemia.

When the pharmaceutical composition of the present invention are employed in the practical prevention or treatment, the dosage of a compound represented by the formula (I) or a prodrug thereof or a pharmaceutically acceptable salt thereof as an active ingredient is appropriately decided depending on the age, sex, body weight, degree of disorders and treatment of each patient and the like, for example, which is approximately within the range of from 1 to 2000 mg per day, more preferably the rage of from 1 to 200 mg per day, per adult human in the case of oral administration, and approximately within the range of from 0.5 to 1000 mg per day, more preferably the rage of from 0.5 to 100 mg per day, per adult human in the case of parenteral administration, and the daily dose can be divided into one to several doses per day and administered.

When the pharmaceutical composition of the present invention are employed in the practical prevention or treatment, various dosage forms are orally or parenterally used depending on their uses, for example, formulations for oral administration such as powders, fine granules, granules, tablets, capsules, dry syrups or the like are preferable.

These pharmaceutical compositions can be prepared depending on their formulations optionally by admixing an appropriate pharmaceutical additive such as excipients, disintegrators, binders, lubricants and the like in accordance with conventional pharmaceutical methods.

For example, powders can be formulated by, if desired, admixing well an active ingredient with appropriate excipients, lubricants and the like. For example, tablets can be formulated by tableting an active ingredient with appropriate excipients, disintegrators, binders, lubricants and the like in accordance with conventional methods, further if desired, can be suitably coated to provide film-coated tablets, sugar-coated tablets, enteric-coated tablets and the like. For example, capsules can be formulated by admixing well an active ingredient with appropriate excipients, lubricants and the like, or formulating fine granules, granules in accordance with conventional methods, and filling it in appropriate capsules. Furthermore, in the case of such a formulation for oral administration drug, it can be also formulated by conducting quick-release or sustained-release formulation depending on the preventions or the treatment methods.

A compound represented by the formula (I) of the present invention, or a prodrug thereof or a pharmaceutically acceptable salt thereof can be used further in combination with any other drug for the treatment of hyperuricemia or drug for the treatment of gout. As the other drug for the treatment of hyperuricemia which can be used in the present invention, for example, urinary alkalizers such as sodium hydrogen carbonate, potassium citrate, sodium citrate and the like can be illustrated. In addition, as the other drug for the treatment of gout, colchicine, or non-steroidal anti-inflammatory drugs such as indomethacin, naproxen, fenbufen, pranoprofen, oxaprozin, ketoprofen, etoricoxib, tenoxicam and the like and steroids and the like can be illustrated. When used in combination with any other drug for the treatment of hyperuricemia or drug for the treatment of gout, not only a single pharmaceutical composition comprising the same together with the active ingredient of the present invention can be used but also a pharmaceutical composition prepared separately from a pharmaceutical composition comprising an active ingredient of the present invention may be used in combination for simultaneous administration or administration at different dosage intervals. Furthermore, when used in combination with any drug other than the active ingredient of the present invention, the dosage of a compound of the present invention can be reduced depending on the dosage of the other drug, as the case may be, an advantageous effect more than an additive effect in the prevention or treatment of the above diseases can be obtained, or an adverse effect of the other drug used in combination can be avoided or declined.

As one of the embodiments in the present invention, the (aza)indolizine derivative represented by the formula (I) is a compound wherein preferably 0 or one of $X^1$ to $X^4$ is a nitrogen atom, and more preferably one of $X^1$ to $X^4$ is a nitrogen atom, and more specifically, a compound represented by the formula (Ia) to (Ii) is preferable, a compound represented by the formula (Ia) to (Ih) is more preferably, a compound represented by the formula (Ia) or (Ih) is even more preferable.

Ring U is preferably a benzene ring, a pyridine ring or a thiazole ring, and more preferably a benzene ring.

In $(R^2)_m$, m is preferably 0, or m is 1 and $R^2$ is a fluorine atom, a hydroxy group, amino, methyl or trifluoromethyl; more preferably m is 0, or m is 1 and $R^2$ is a fluorine atom, a hydroxy group or amino; and even more preferably m is 0, or m is 1 and $R^2$ is a hydroxy group; and even more preferably m is 1 and $R^2$ is a hydroxy group.

$R^1$ is preferably independently any one of the following (a1) to (a4):
(a1) a hydrogen atom;
(a2) a halogen atom;
(a3) a hydroxy group;
(a4) $C_{1-6}$ alkyl, $C_{1-6}$ alkoxy, mono(di)$C_{1-6}$ alkylamino, $C_{2-7}$ acyl, $C_{3-8}$ cycloalkyl, 3 to 8-membered heterocycloalkyl, $C_6$ aryl or 5 or 6-membered heteroaryl each of which may have any group selected from substituent group G;
and more preferably independently any one of the following (b 1) to (b4):
(b1) a hydrogen atom;
(b2) a halogen atom;
(b3) a hydroxy group;
(b4) $C_{1-6}$ alkyl, $C_{1-6}$ alkoxy, mono(di)$C_{1-6}$ alkylamino or hydroxy$C_{1-6}$ alkyl each of which may be substituted by a fluorine atom; and more specifically, $R^{1a}$ is more preferably a hydrogen atom or a halogen atom, and even more preferably a hydrogen atom, a chlorine atom or a fluorine atom.

$R^{1b}$ is more preferably a hydrogen atom, a halogen atom, $C_{1-6}$ alkyl or $C_{1-6}$ alkoxy, and even more preferably a hydrogen atom, a fluorine atom, methyl, ethyl and methoxy.

$R^{1c}$ is more preferably a hydrogen atom, a halogen atom, $C_{1-6}$ alkyl or $C_{1-6}$ alkyl which may have a fluorine atom or a chlorine atom as substituent group G, and even more preferably a hydrogen atom, a fluorine atom, a chlorine atom, methyl or trifluoromethyl.

Also, as one of the embodiments in the present invention, in the (aza)indolizine derivative represented by the formula (II), ring U is preferably a benzene ring, a pyridine ring or a thiazole ring, and more preferably a benzene ring.

$R^3$ is preferably independently any one of the following (c1) to (c4):
(c1) a hydrogen atom;
(c2) a halogen atom;
(c3) a hydroxy group;
(c4) $C_{1-6}$ alkyl, $C_{1-6}$ alkoxy, mono(di)$C_{1-6}$ alkylamino, $C_{2-7}$ acyl, $C_{3-8}$ cycloalkyl, 3 to 8-membered heterocycloalkyl, $C_6$ aryl or 5 or 6-membered heteroaryl each of which may have any group selected from substituent group G;
and more preferably independently any one of the following (d1) to (d4):
(d1) a hydrogen atom;
(d2) a halogen atom;
(d3) a hydroxy group;
(d4) $C_{1-6}$ alkyl, $C_{1-6}$ alkoxy, mono(di)$C_{1-6}$ alkylamino or hydroxy$C_{1-6}$ alkyl each of which may be substituted by a fluorine atom; and more specifically, $R^{3a}$ is more preferably a hydrogen atom or a halogen atom, and even more preferably a hydrogen atom, a chlorine atom or a fluorine atom.

$R^{3b}$ is more preferably a hydrogen atom, a halogen atom, $C_{1-6}$ alkyl or $C_{1-6}$ alkoxy, and even more preferably a hydrogen atom, a fluorine atom, methyl, ethyl or methoxy.

$R^{3c}$ is more preferably a hydrogen atom, a halogen atom, $C_{1-6}$ alkyl or $C_{1-6}$ alkyl which may have a fluorine atom or a chlorine atom as substituent group G, and even more preferably a hydrogen atom, a fluorine atom, a chlorine atom, methyl or trifluoromethyl.

Also, as one of the embodiments in the present invention, in the (aza)indolizine derivatives represented by the formula (I), a compound having URAT1 inhibitory activity is preferred.

As such a compound, for example, an (aza)indolizine derivative represented by the following general formula (IIA):

[Chem. 18]

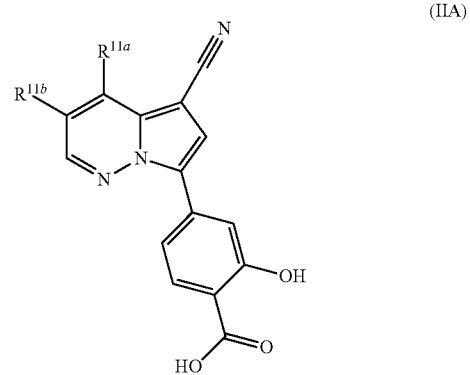

(IIA)

wherein
$R^{11a}$ is a hydrogen atom, a chlorine atom or a fluorine atom; and
$R^{11b}$ is a hydrogen atom, methyl or methoxy;
an (aza)indolizine derivative represented by the following general formula (IIB):

[Chem. 19]

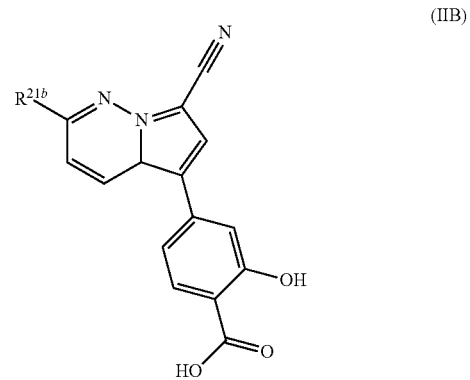

(IIB)

wherein
$R^{21b}$ is a hydrogen atom, methyl or methoxy;
an indolizine derivative represented by the following general formula (IC):

[Chem. 20]

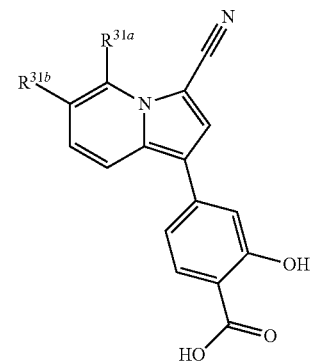

(IC)

wherein

R$^{31a}$ is a hydrogen atom, a chlorine atom, a fluorine atom or methyl; and

R$^{31b}$ is a hydrogen atom, methyl or methoxy;

and the like can be illustrated.

In this description, what is described in an (aza)indolizine derivative represented by the formula (I) is the same for an azaindole derivative represented by the formula (III) unless otherwise specified.

Effect of the invention

The (aza)indolizine derivatives represented by the formula (I) of the present invention exert an excellent xanthine oxidase inhibitory activity and suppress the production of uric acid. Therefore, the (aza)indolizine derivatives represented by the formula (I) of the present invention or prodrugs thereof, or pharmaceutically acceptable salts thereof can extremely suppress an increase in serum uric acid level and are useful as an agent for the prevention or treatment of diseases associated with abnormal serum uric acid level such as hyperiuricemia or the like.

Mode to Operate the Invention

The present invention is further illustrated in more detail by way of the following Reference Examples, Examples and Test Examples. However, the present invention is not limited thereto.

REFERENCE EXAMPLE 1

2-Methoxymethoxy-4-(4,4,5,5-tetramethyl-[1,3,2]dioxaborolane-2-yl)benzoic acid methyl ester To a solution of 4-iodo-2-methoxymethoxy benzoic acid methyl ester (1.29 g) in N,N-dimethylformamide (10 mL) were added bis(pinacolato)diboron (1.12 g), palladium acetate (II) (0.05 g) and potassium acetate (1.18 g) at room temperature, and the mixture was stirred at 80° C. for 8 hours. After cooling to ambient temperature, to the reaction mixture was added water, and the resulting mixture was extracted with toluene. The organic layer was washed with brine, dried over anhydrous magnesium sulfate and concentrated under reduced pressure. The residue was purified by column chromatography on silica gel (eluent: n-hexane/ethyl acetate) to give the title compound (0.52 g).

REFERENCE EXAMPLE 2

5-Bromopyrrolo[1,2-b]pyridazine-7-carbonitrile

To a solution of pyridazine (1.10 g) in tetrahydrofuran (30 mL) was added tetracyanoethylene oxide (2.00 g) at 0° C., and the mixture was stirred at the same temperature overnight. The mixture was concentrated under reduced pressure, and the obtained solid was washed with dichloromethane and dried under reduced pressure at 50° C. To a suspension of the obtained solid (1.90 g) in toluene (30 mL) was added bis(trimethylsilyl)acetylene (22.9 g) at room temperature, and the mixture was heated under reflux for 2 days. The mixture was concentrated under reduced pressure, and the residue was purified by column chromatography on silica gel (eluent: n-hexane/ethyl acetate) to give a mixture (1.60 g) of 5,6-bistrimethylsilanylpyrrolo[1,2-b]pyridazine-7-carbonitrile and 5-trimethylsilanylpyrrolo[1,2-b]pyridazine-7-carbonitrile. To a solution of the obtained mixture (1.60 g) in tetrahydrofuran (25 mL) was added 1 mol/L solution of tetra-n-butyl ammonium fluoride in tetrahydrofuran (5.7 mL) under ice-cooling, and the mixture was stirred at room temperature overnight. To the reaction mixture was added water, and the resulting mixture was extracted with dichloromethane. The organic layer was dried over anhydrous magnesium sulfate, and concentrated under reduced pressure to give pyrrolo[1,2-b]pyridazine-7-carbonitrile (1.10 g). To a solution of the obtained compound (1.10 g) in dichloromethane (30 mL) was added N-bromosuccinimide (1.50 g) at room temperature, and the mixture was stirred at the same temperature for 3 hours. To the mixture was added 1 mol/L sodium thiosulfate aqueous solution. The resulting mixture was extracted with dichloromethane, and concentrated under reduced pressure. The residue was purified by column chromatography on silica gel (eluent: n-hexane/ethyl acetate) to give the title compound (1.23 g).

REFERENCE EXAMPLE 3

5-Bromo-2-methylpyrrolo[1,2-b]pyridazine-7-carbonitrile

The title compound was prepared in a similar manner to that described in Reference Example 2 using the corresponding starting materials.

REFERENCE EXAMPLE 4

5-Bromo-2-chloro-3-methylpyrrolo[1,2-b]pyridazine-7-carbonitrile

The title compound was prepared in a similar manner to that described in Reference Example 2 using the corresponding starting materials.

REFERENCE EXAMPLE 5

5-Bromo-2-chloropyrrolo[1,2-b]pyridazine-7-carbonitrile

The title compound was prepared in a similar manner to that described in Reference Example 2 using the corresponding starting materials.

REFERENCE EXAMPLE 6

5-Bromo-2-methoxypyrrolo[1,2-b]pyridazine-7-carbonitrile

The title compound was prepared in a similar manner to that described in Reference Example 2 using the corresponding starting materials.

REFERENCE EXAMPLE 7

1-Bromoindolizine-3-carbonitrile

To a solution of pyridine (2.00 g) in ethyl acetate (20 mL) was added bromoacetonitrile (3.64 g) at room temperature, and the mixture was heated under reflux overnight. The precipitated solid was collected by filtration, washed with ethyl acetate and dried under reduced pressure at 50° C. To a suspension of the obtained compound (4.9 g) in chlorobenzene (30 mL) were added benzyl acrylate (7.99 g), manganese dioxide (10.70 g) and triethylamine (2.49 g) at room temperature, and the mixture was stirred at 80° C. for 5 hours. The mixture was filtered through a Celite pad, and the filtrate was concentrated. The residue was purified by column chromatography on silica gel (eluent: n-hexane/ethyl acetate) to give 3-cyanoindolizine-1-carboxylic acid benzyl ester (4.90 g). To a mixed solution of the obtained compound (2.50 g) in methanol (15 mL) and tetrahydrofuran (15 mL) was added palladium 10% on carbon (wetted with ca. 50% water) (0.25 g), and the mixture was stirred under a hydrogen atmosphere at room temperature overnight. To the mixture was added 1 mol/L sodium hydroxide aqueous solution, and the resulting mixture was extracted with ether. To the aqueous layer was added 2 mol/L hydrochloric acid, and the precipitated solid was collected by filtration. The obtained solid was dried under reduced pressure at 50° C. to give 3-cyanoindolizine-1-carboxylic acid (0.63 g). To a suspension of the obtained compound (0.63 g) in quinoline (5 mL) was added copper (0.05 g), and the mixture was stirred at 220° C. for 45 minutes. To the mixture was added 2 mol/L hydrochloric acid, and the mixture was extracted with ethyl acetate. The organic layer was washed with 1 mol/L hydrochloric acid and brine, dried over anhydrous magnesium sulfate and concentrated under reduced pressure. The residue was purified by column chromatography on silica gel (eluent: n-hexane/ethyl acetate) to give indolizine-3-carbonitrile (0.23 g). To a solution of the obtained compound (0.23 g) in dichloromethane (5 mL) was added N-bromosuccinimide (0.37 g) at room temperature, and the mixture was stirred at same temperature for 2 hours. To the reaction mixture was added 1 mol/L sodium thiosulfate aqueous solution, and the resulting mixture was extracted with dichloromethane. The organic layer was concentrated under reduced pressure. The residue was purified by column chromatography on silica gel (eluent: n-hexane/ethyl acetate) to give the title compound (0.30 g).

REFERENCE EXAMPLE 8

1-Bromo-6-fluoroindolizine-3-carbonitrile

The title compound was prepared in a similar manner to that described in Reference Example 7 using the corresponding starting materials.

REFERENCE EXAMPLE 9

7-Bromopyrrolo[1,2-b]pyridazine-5-carbonitrile

To a solution of pyridazine (25 g) in ethyl acetate (200 ml) was added bromoacetic acid (52 g) at room temperature, and the mixture was stirred at 80° C. overnight. The mixture was concentrated under reduced pressure. The precipitated solid was collected by filtration, and dried under reduced pressure. To a suspension of the obtained compound (17 g) in chlorobenzene (160 mL) were added acrylonitrile (8.28 g), manganese dioxide (33 g) and triethylamine (7.89 g), and the mixture was stirred at 80° C. for 5 hours. The reaction mixture was filtered through a Celite pad, and the filtrate was concentrated under reduced pressure. The residue was purified by column chromatography on silica gel (eluent: n-hexane/ethyl acetate) to give pyrrolo[1,2-b]pyridazine-5-carbonitrile (0.30 g). To a solution of the obtained compound (0.30 g) in dichloromethane (10 mL) was added N-bromosuccinimide (0.41 g) at room temperature, and the mixture was stirred at same temperature for 3 hours. To the mixture was added 1 mol/L sodium thiosulfate aqueous solution, and the resulting mixture was extracted with dichloromethane. The organic layer was concentrated under reduced pressure. The residue was purified by column chromatography on silica gel (eluent: n-hexane/ethyl acetate) to give the title compound (0.20 g).

REFERENCE EXAMPLE 10

4-(5-Cyano-4-methyl pyrrolo[1,2-b]pyridazine-7-yl)benzoic acid methyl ester

To a solution of 4-methyl pyridazine (1.00 g) in ethyl acetate (30 ml) was added 4-bromomethyl benzoic acid methyl ester (2.92 g) at room temperature, and the mixture was stirred at 80° C. overnight. The precipitated solid was collected by filtration, washed with ethyl acetate and dried under reduced pressure. To a solution of the obtained compound (4.50 g) in 1,2-dimethoxyethane (26 mL) were added acrylonitrile (3.69 g), manganese dioxide (6.05 g) and triethylamine (4.22 g) at room temperature, and the mixture was stirred at 80° C. for 7 hours. The mixture was filtered through a Celite pad, and the filtrate was concentrated under reduced pressure. The residue was purified by column chromatography on silica gel (eluent: n-hexane/ethyl acetate) to give the title compound (0.330 g).

REFERENCE EXAMPLE 11

4-(8-Cyanopyrrolo[1,2-a]pyrazine-6-yl)benzoic acid methyl ester

The title compound was prepared in a similar manner to that described in Reference Example 10 using the corresponding starting materials.

REFERENCE EXAMPLE 12

8-Bromopyrrolo[1,2-a]pyrazine-6-carbonitrile

The title compound was prepared in a similar manner to that described in Reference Example 2 using the corresponding starting materials.

REFERENCE EXAMPLE 13

4-(3-Cyanopyrrolo[3,2-b]pyridine-1-yl)-2-methoxymethoxy benzoic acid ethyl ester To a solution of 1H-pyrrolo[3,2-b]pyridine (0.4 g) in N,N-dimethylformamide (6 mL) were added 4-fluoro-2-methoxymethoxy benzoic acid ethyl ester (0.85 g) and cesium carbonate (2.21 g) at room temperature, and the mixture was stirred at 80° C. overnight. To the mixture was added water, and the resulting mixture was extracted with dichloromethane. The organic layer was concentrated under reduced pressure. The residue was purified by column chromatography on silica gel (eluent: n-hexane/ethyl acetate) to give 2-methoxymethoxy-4-pyrrolo[3,2-b]pyridine-1-yl-benzoic acid ethyl ester (0.60 g). To a solution of the obtained compound (0.60 g) in dichloromethane (30 mL) was added N-bromosuccinimide (0.33 g) under ice-cooling, and the mixture was stirred at the same temperature for 2 hours. To the mixture was added 1 mol/L sodium thiosulfate aqueous solution. The resulting mixture was extracted with dichloromethane, and concentrated under reduced pressure. The residue was purified by column chromatography on silica gel (eluent: n-hexane/ethyl acetate) to give 4-(3- bromopyrrolo[3,2-b]pyridine-1-yl)-2-methoxymethoxy benzoic acid ethyl ester (0.49 g). To a solution of the obtained compound (0.49 g) in N-methylpyrrolidone (10 mL) were added zinc cyanide and tetrakis (triphenylphosphine) palladium (0) (0.28 g) at room temperature, and the mixture was stirred at 150° C. for 1 hour using microwave reactor. To the reaction mixture was added water, and the resulting mixture was extracted with ethyl acetate. The organic layer was concentrated under reduced pressure. The residue was purified by column chromatography on silica gel (eluent: n-hexane/ethyl acetate) to give the title compound (0.25 g).

EXAMPLE 1

4-(7-Cyanopyrrolo[1,2-b]pyridazine-5-yl)benzoic acid

To a mixed solution of 5-bromopyrrolo[1,2-b]pyridazine-7-carbonitrile (0.022 g) in 1,2-dimethoxyethane (2 mL) and water (0.3 mL) were added 4-methoxycarbonyl phenyl boronic acid (0.020 g), tetrakis(triphenylphosphine)palladium (0) (0.006 g) and cesium carbonate (0.048 g) at room temperature, and the mixture was stirred at 80° C. under an argon atmosphere for 3 hour. To the mixture was added water, and the resulting mixture was extracted with ethyl acetate. The organic layer was washed with water, dried over anhydrous magnesium sulfate and concentrated under reduced pressure. The residue was purified by column chromatography on silica gel (eluent: n-hexane/ethyl acetate=95/5-10/90) to give 4-(7-cyanopyrrolo[1,2-b]pyridazine-5-yl)benzoic acid methyl ester (0.018 g). To a mixed solution of the obtained compound (0.018 g) in tetrahydrofuran (2 mL), ethanol (1 mL) and water (1 mL) was added lithium hydroxide monohydrate (0.008 g) at room temperature, and the mixture was stirred at same temperature overnight. To the reaction mixture was added 1 mol/L hydrochloric acid, and the precipitated solid was collected by filtration, washed with water and dried under reduced pressure at 50° C. to give the title compound (0.002 g).

EXAMPLE 2

4-(7-Cyanopyrrolo[1,2-b]pyridazine-5-yl)-2-hydroxy benzoic acid

To a mixed solution of 5-bromopyrrolo[1,2-b]pyridazine-7-carbonitrile (0.38 g) in N,N-dimethylformamide (5 mL) and water (0.5 mL) were added 2-methoxymethoxy-4-(4,4,5,5-tetramethyl-[1,3,2]dioxaborolane-2-yl) benzoic acid methyl ester (0.55 g), tetrakis (triphenylphosphine) palladium (0) (0.10 g) and cesium carbonate (0.83 g) at room temperature, and the mixture was stirred at 80° C. for 7 hours. After cooling to room temperature, to the reaction mixture was added water, and the precipitated solid was collected by filtration and purified by column chromatography on silica gel (eluent: n-hexane/ethyl acetate=95/5-10/90) to give 4-(7-cyanopyrrolo[1,2-b]pyridazine-5-yl)-2-methoxymethoxy benzoic acid methyl ester (0.41 g). To a mixed solution of the obtained compound (0.41 g) in tetrahydrofuran (12 mL), ethanol (6 mL) and water (6 mL) was added lithium hydroxide monohydrate (0.24 g), and the mixture was stirred at room temperature for 5 hours. To the reaction mixture was added 2 mol/L hydrochloric acid, and the mixture was stirred at 50° C. overnight. After cooling to room temperature, to the reaction mixture was added water. The precipitated solid was collected by filtration, washed with water and dried under reduced pressure at 50° C. to give the title compound (0.30 g).

EXAMPLES 3 TO 6

The compounds of Examples 3 to 6 were prepared in a similar manner to that described in Example 2 using the corresponding starting materials.

EXAMPLE 7

The compound of Example 7 was prepared in a similar manner to that described in Example 1 using the corresponding starting materials.

EXAMPLES 8 TO 9

The compounds of Examples 8 to 9 were prepared in a similar manner to that described in Example 2 using the corresponding starting materials.

EXAMPLE 10

The compound of Example 10 was prepared in a similar manner to that described in Example 1 using the corresponding starting materials.

EXAMPLE 11

4-(5-Cyano-4-methyl pyrrolo[1,2-b]pyridazine-7-yl)benzoic acid

To a mixed solution of 4-(5-cyano-4-methyl pyrrolo[1,2-b]pyridazine-7-yl)benzoic acid methyl ester (0.35 g) in tetrahydrofuran (7 mL), ethanol (3.5 mL) and water (3.5 mL) was added lithium hydroxide monohydrate (0.14 g) at room temperature, and the mixture was stirred at same temperature overnight. To the mixture was added 1 mol/L hydrochloric acid. The precipitated solid was collected by filtration, washed with water and methanol and dried under reduced pressure at 50° C. to give the title compound (0.088 g).

EXAMPLE 12

The compound of Example 12 was prepared in a similar manner to that described in Example 2 using the corresponding starting materials.

EXAMPLE 13

The compound of Example 13 was prepared in a similar manner to that described in Example 11 using the corresponding starting materials.

EXAMPLE 14

4-(6-Cyanopyrrolo[1,2-a]pyrazine-8-yl)-2-hydroxy benzoic acid

To a mixed solution of 8-bromopyrrolo[1,2-a]pyrazine-6-carbonitrile (0.038 g) in N,N-dimethylformamide (2 mL) and water (0.2 mL) were added 2-methoxymethoxy-4-(4,4,5,5-tetramethyl-[1,3,2]dioxaborolane-2-yl)benzoic acid methyl ester (0.066 g), tetrakis (triphenylphosphine) palladium (0) (0.01 g) and cesium carbonate (0.084 g) at room temperature, and the mixture was stirred at 80° C. for 6 hours. After cooling to room temperature, to the reaction mixture was added water, and the resulting mixture was extracted with ethyl acetate. The organic layer was washed with brine, dried over anhydrous magnesium sulfate and concentrated under reduced pressure. The residue was purified by column chromatography on silica gel (eluent: n-hexane/ethyl acetate=95/5-10/90) to give 4-(6-cyanopyrrolo[1,2-a]pyazine-8-yl)-2-methoxymethoxy benzoic acid methyl ester (0.016 g). To a mixed solution of the obtained compound (0.016 g) in tetrahydrofuran (2 mL), ethanol (1 mL) and water (1 mL) was added lithium hydroxide monohydrate (0.01 g), and the mixture was stirred at room temperature for 4 hours. To the reaction mixture was added 2 mol/L hydrochloric acid, and the mixture was stirred at 50° C. overnight. After cooling to room temperature, to the reaction mixture was added water. The precipitated solid was collected by filtration, washed with water and dried under reduced pressure at 50° C. to give 4-(6-carbamoyl pyrrolo[1,2-a]pyrazine-8-yl)-2-hydroxy benzoic acid (0.013 g). To a solution of the obtained solid (0.01 g) in dichloromethane were added trifluoroacetic anhydride (0.035 g) and triethylamine (0.027 g) under ice-cooling, and the mixture was stirred at room temperature overnight. To the mixture was added methanol, and the mixture was stirred for 30 minutes. The solvent was concentrated under reduced pressure, and the residue was purified by column chromatography on silica gel (eluent: methanol/dichloromethane=30/70-50/50). To the obtained solid were added ethyl acetate and 1 mol/L hydrochloric acid, and the organic layer was concentrated under reduced pressure to give the title compound (0.001 g).

EXAMPLE 15

4-(3-Cyanopyrrolo[3,2-b]pyridine-1-yl)-2-hydroxy benzoic acid

To a mixed solution of 4-(3-cyanopyrrolo[3,2-b]pyridine-1-yl)-2-methoxymethoxy benzoic acid ethyl ester (0.25 g) in tetrahydrofuran (7.2 mL), ethanol (3.6 mL) and water (3.6 mL) was added lithium hydroxide monohydrate (0.15 g), and the mixture was stirred at room temperature for 5 hours. To the reaction mixture was added 2 mol/L hydrochloric acid, and the mixture was stirred at 50° C. overnight. After cooling to room temperature, to the reaction mixture was added water. The precipitated solid was collected by filtration, washed with water and dried under reduced pressure at 50° C. to give the title compound (0.15 g).

EXAMPLE 16

The compound of Example 16 was prepared in a similar manner to that described in Example 2 using the corresponding starting materials.

Tables 1 to 3 show the chemical structures and $^1$H-NMR data of the above compounds of Examples 1 to 16.

The abbreviations in these Tables: "Ex No." and "Str.", represent Example number and chemical structure, respectively.

TABLE 1

| Ex. No. | Str. | $^1$H-NMR δ ppm (DMSO-d6) |
|---|---|---|
| 1 | *(structure)* | 7.10-7.30 (1H, m), 7.70-8.05 (4H, m), 8.08 (1H, s), 8.45-8.65 (2H, m) |
| 2 | *(structure)* | 7.15-7.95 (4H, m), 8.09 (1H, s), 8.45-8.70 (2H, m) |

TABLE 1-continued

| Ex. No. | Str. | ¹H-NMR δ ppm (DMSO-d6) |
|---|---|---|
| 3 | | 2.56 (3H, s), 7.12 (1H, d, J = 9.5 Hz), 7.20-7.35 (2H, m), 7.80-7.95 (1H, m), 7.99 (1H, s), 8.40 (1H, d, J = 9.5 Hz) |
| 4 | | 2.20-2.35 (3H, m), 7.05-7.25 (2H, m), 7.89 (1H, s), 7.90-8.20 (2H, m) |
| 5 | | 7.55-7.70 (2H, m), 7.75-8.05 (3H, m), 8.15-8.30 (1H, m) |

TABLE 2

| Ex. No. | Str. | ¹H-NMR δ ppm (DMSO-d6) |
|---|---|---|
| 6 | | 4.00 (3H, s), 6.80-7.30 (3H, m), 7.75-8.45 (3H, m) |
| 7 | | 7.00-7.40 (2H, m), 7.60-8.20 (6H, m), 8.45-8.65 (1H, m) |

TABLE 2-continued
| Ex. No. | Str. | ¹H-NMR δ ppm (DMSO-d6) |
|---|---|---|
| 8 | | 7.00-7.45 (4H, m), 7.75-8.15 (3H, m), 8.45-8.65 (1H, m) |
| 9 | | 7.10-7.45 (3H, m), 7.75-8.15 (3H, m), 8.70-8.85 (1H, m) |
| 10 | | 7.15-7.35 (1H, m), 7.99 (1H, s), 8.00-8.45 (5H, m), 8.55-8.70 (1H, m), 13.05 (1H, brs) |
TABLE 3
| Ex. No. | Str. | ¹H-NMR δ ppm (DMSO-d6) |
|---|---|---|
| 11 | 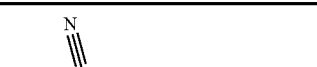 | 2.74 (3H, s), 7.08 (1H, d, J = 4.6 Hz), 7.93 (1H, s), 7.95-8.30 (4H, m), 8.51 (1H, d, J = 4.6 Hz), 13.03 (1H, brs) |

TABLE 3-continued

| Ex. No. | Str. | ¹H-NMR δ ppm (DMSO-d6) |
|---|---|---|
| 12 | | 7.20-7.90 (4H, m), 8.03 (1H, s), 8.30-8.70 (2H, m) |
| 13 | | 7.78 (1H, s), 7.80-8.20 (5H, m), 8.50-8.65 (1H, m), 9.15-9.30 (1H, m), 13.18 (1H, brs) |
| 14 | | 7.25-7.45 (2H, m), 7.80-8.20 (3H, m), 8.45-8.65 (1H, m), 9.30-9.50 (1H, m) |
| 15 | | 7.20-7.50 (3H, m), 7.95-8.25 (2H, m), 8.55-8.70 (1H, m), 8.90-9.05 (1H, m) |
| 16 | | 2.34 (3H, s), 2.90 (3H, s), 7.05-7.30 (3H, m), 7.75-7.90 (2H, m), 7.95 (1H, s) |

TEST EXAMPLE 1

Xanthine Oxidase Inhibitory Activity (1) Preparation of Test Compounds

Test compounds were dissolved in dimethyl sulfoxide (DMSO) (manufactured by Wako pure chemical) at 40 mM concentration and then diluted to intended concentrations with phosphate-buffered saline (PBS).

(2) Method of Measurement

Xanthine oxidase (from bovine milk, manufactured by Sigma) was prepared with phosphate-buffered saline (PBS) at 0.02 units/mL, and then the solution was added to 96-well plates at 50 μL/well. In addition, test compounds diluted with PBS were added at 50 μL/well. Xanthine (manufactured by Wako pure chemical) at 200 μM prepared with PBS was added at 100 μL/well, and the reaction was conducted for 10 minutes at room temperature. Absorbance at 290 nm was measured by using a microplate reader SpectraMax Plus 384 (manufactured by Molecular device). The absorbance under a condition without xanthine is 0%, and control without test compounds is 100%. Fifty % inhibitory concentration of a test compound ($IC_{50}$) was calculated (Table 4). "Ex. No" in the table indicates Example number.

TABLE 4

| Ex. No. | $IC_{50}$ (nM) |
|---|---|
| 1 | 7 |
| 2 | 5 |
| 3 | 5 |
| 6 | 3 |
| 7 | 8 |
| 8 | 12 |
| 9 | 4 |
| 10 | 12 |
| 11 | 10 |
| 12 | 4 |
| 15 | 10 |
| 16 | 13 |

TEST EXAMPLE 2

Inhibitory Activity of Uric Acid Transport with Human URAT1-Expressing Cells (1) Cells Used in the Test URAT1-expressing HEK293 cells (HEK293 cells transfected with vector containing human URAT1 cDNA) and control cells (HEK293 cells transfected with vector alone) were used.

URAT1-expressing cells and control cells were seeded in collagen I-coated 24-well plates (manufactured by BD FALCON) at 1 to $4 \times 10^5$ cells/well, and cultured in $CO_2$ incubator (37° C., $CO_2$: 5%) for 1 to 3 days, and then the following measurement of uric acid transport was conducted. In addition, Dulbecco's Modified Eagle Medium (manufactured by Invitrogen) containing 9% fetal bovine serum (manufactured by Invitrogen), antibiotic-antimycotic (manufactured by Invitrogen) and 2 mmol/L L-glutamine were used for the culture.

(2) Preparation of Test Compounds $^{14}$C-labeled uric acid ($^{14}$C uric acid) (manufactured by American Radiolabeled Chemicals, Inc.) was dissolved in Hanks' balanced salt solution (HBSS) (manufactured by Invitrogen) to prepare HBSS containing $^{14}$C uric acid at 50 μM. Test compounds were dissolved in DMSO and then diluted to 1000-fold with the prepared HBSS containing $^{14}$C uric acid above to prepare $^{14}$C uric acid solution containing the indicated concentration of test compounds (final concentration of DMSO: 0.1%). $^{14}$C uric acid solution containing 0.1% DMSO was prepared as a control.

(3) Measurement of Uric Acid Transport

After the medium was removed from the plates in which cells were seeded, and 1 mL of HBSS was added to the cells. After the HBSS was removed, 0.3 mL of HBSS was newly added to the cells, which were incubated at 37° C. for 15 minutes. After the HBSS was removed, 0.3 mL of $^{14}$C uric acid solution containing 0.1% DMSO or test compounds was added to the cells, which were then incubated at 37° C. for 2 minutes. After the incubation, the solution was removed, and the cells were washed once with 1 mL of ice-cold phosphate-buffered saline containing 0.2% BSA, and washed twice with 1 mL of ice-cold PBS. After the PBS was removed, the cells were lysed by addition of 0.5 mL of 0.1 mol/L NaOH aqueous solution for each well. The cell lysates (0.3 mL/well) were transferred into glass vials, and mixed with 10 mL of a scintillator (Hionic-Fluor, manufactured by Perkin Elmer). The radioactivity was measured by means of a liquid scintillation counter.

(4) Protein Determination

Protein concentration in the cell lysates was determined by BCA Protein Assay Kit (manufactured by Pierce) and then amount of protein (mg/well) was calculated.

(5) Calculation of the Percent Inhibition of Uric Acid Uptake for Each Compound

Uric acid uptake activity in each well was calculated by the following formula.

Uric acid uptake activity (p mol/mg protein)=radioactivity (dpm/well)/[amount of protein (mg/well)×concentration of radioactivity in HBSS containing $^{14}$C uric acid (dpm/p mol)]

Percent inhibition was calculated according to the following formula.

Percent inhibition (%)=[1−(B−C)/(A−C)]×100

A: Uric acid uptake activity in URAT1-expressing HEK293 cells in the presence of 0.1% DMSO B: Uric acid uptake activity in URAT1-expressing HEK293 cells in the presence of test compounds C: Uric acid uptake activity in control cells in the presence of 0.1% DMSO (6) Results The compounds of Examples 2, 3, 6, 8, 9, 12 and 16 showed not less than 50 percent inhibition in a concentration of 10 μM.

TEST EXAMPLE 3

Hypouricemic Effect (1) Method of Measurement

Test compounds (1 mg/kg) suspended in 0.5% methylcellulose solution were orally administered to overnight fasted male CD (SD) IGS rats (5-week-old, Charles River Japan). At 2 hours after administration, blood was collected under ether anesthesia from abdominal aorta, and serum was separated according to a general method. Serum uric acid levels were determined by use of uric acid measurement kit (Uric acid C-Test Wako: manufactured by Wako pure chemical), and percent decrease in uric acid was calculated according to the formula described below.

Percent decrease in uric acid (%)=(Serum uric acid levels in control animals−Serum uric acid levels in animals administered test compounds)×100/ Serum uric acid levels in control animals (2) Results Oral administration of test compounds of Examples 2 and 12 at 3 mg/kg showed not less than 60 percent decrease in uric acid.

Oral administration of a test compound of Example 3 at 1 mg/kg showed not less than 60 percent decrease in uric acid.

TEST EXAMPLE 4

Acute Toxicity Test

Test compounds of Examples 2 and 12 (300 mg/kg) suspended in 0.5% methylcellulose solution were orally administered to male ICR mice (7-week-old, 5 mice per group), and the general condition during 24 hours after administration was observed. As a result, there were no deaths, and no abnormalities in general conditions were observed.

Industrial Applicability

The (aza)indolizine derivatives represented by the formula (I) of the present invention or prodrugs thereof, or pharmaceutically acceptable salts thereof exert an excellent xanthine oxidase inhibitory activity, and therefore, can exert an inhibitory activity of uric acid production and lower serum uric acid level. Therefore, the present invention can provide an agent for the prevention or treatment of hyperuricemia, gouty tophus, gouty arthritis, renal disorder associated with hyperuricemia, urinary calculi or the like.

The invention claimed is:

1. A compound represented by the formula (I):

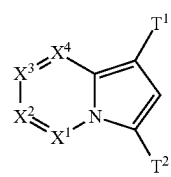

(I)

wherein 0 to 2 of $X^1$, $X^2$, $X^3$ and $X^4$ are a nitrogen atom and the others are $CR^1$;

one of $T^1$ and $T^2$ represents cyano and the other represents a group represented by the formula:

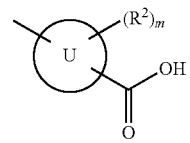

and with the proviso that when $T^1$ is cyano, at least one of $X^1$ to $X^4$ is a nitrogen atom;

$R^1$ independently represents any one of the following (1) to (8):

(1) a hydrogen atom;
(2) a halogen atom;
(3) a hydroxy group;
(4) amino;
(5) carbamoyl;
(6) cyano;
(7) carboxy;
(8) $C_{1-6}$ alkyl, $C_{2-6}$ alkenyl, $C_{2-6}$ alkynyl, $C_{1-6}$ alkoxy, mono(di)$C_{1-6}$ alkylamino, $C_{2-7}$ acyl, $C_{2-7}$ acylamino, mono(di)$C_{1-6}$ alkylcarbamoyl, $C_{1-6}$ alkylsulfonyl, $C_{1-6}$ alkylsulfonylamino, mono(di)$C_{1-6}$ alkylsulfamoyl, $C_{1-6}$ alkylthio, $C_{3-8}$ cycloalkyl, 3 to 8-membered heterocycloalkyl, $C_{5-8}$ cycloalkenyl, 5 to 8-menbered heterocycloalkenyl, $C_{3-8}$ cycloalkyloxy, $C_{3-8}$ cycloalkylamino, $C_6$ aryl, 5 or 6-membered heteroary, $C_6$ aryloxy, $C_6$ arylamino, $C_6$ arylcarbonyl or $C_6$ arylcarbonylamino each of which may have any group selected from substituent group G;

substituent group G consists of a fluorine atom, a chlorine atom, a hydroxy group, amino, carboxy, carbamoyl, cyano, $C_{1-6}$ alkyl, $C_{1-6}$ alkoxy and mono(di)$C_{1-6}$ alkylamino;

ring U represents a benzene ring;

m represents an integral number from 0 to 2; and $R^2$ represents a fluorine atom, a hydroxy group, amino, methyl or trifluoromethyl, and when m is 2, two $R^2$ are optionally different from each other, or a pharmaceutically acceptable salt thereof.

2. The compound as claimed in claim 1 wherein the compound, represented by the (I) is a compound, represented by the following formula (Ia) to (Ii):

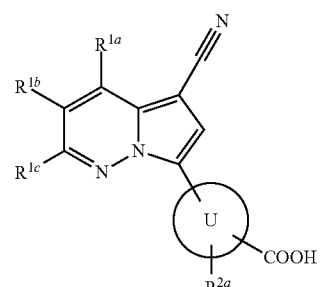

(Ia)

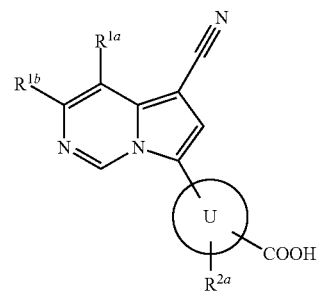

(Ib)

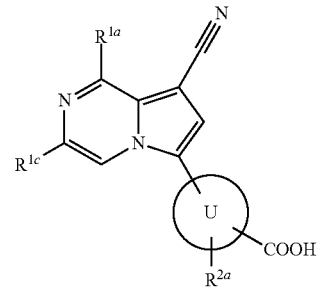

(Ic)

-continued (Id)
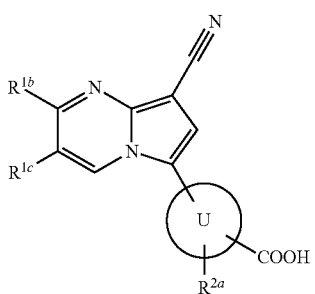

(Ie)
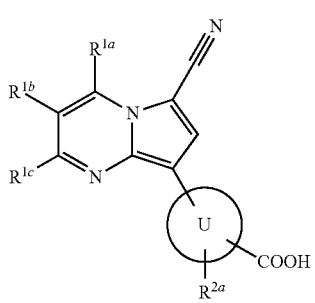

(If)
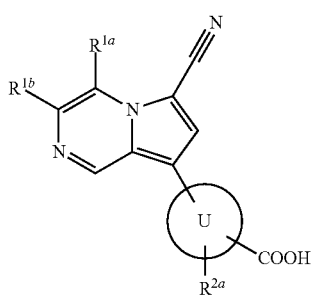

(Ig)
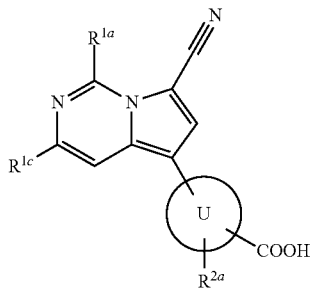

(Ih)
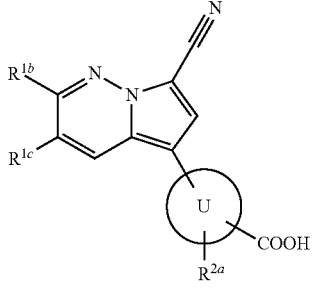

-continued (Ii)
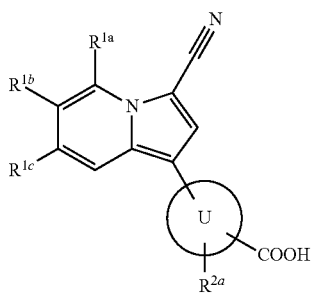

wherein $R^{1a}$, $R^{1b}$ and $R^{1c}$ independently represent any one of the following (a1) to (a4):

(a1) a hydrogen atom;

(a2) a halogen atom;

(a3) a hydroxy group;

(a4) $C_{1-6}$ alkyl, $C_{1-6}$ alkoxy, mono(di)$C_{1-6}$ alkylamino, $C_{2-7}$ acyl, $C_{3-8}$ cycloalkyl, 3 to 8-membered heterocycloalkyl, $C_6$ aryl or 5 or 6-membered heteroaryl each of which may have any group selected from substituent group G;

$R^{2a}$ represents a hydrogen atom, a fluorine atom, a hydroxy group or amino; and ring U and substituent group G have the same meanings as defined in claim 1, or a pharmaceutically acceptable salt thereof.

3. The compound as claimed in claim 2, wherein the group represented by the formula:

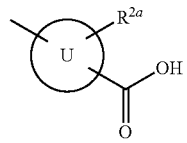

is a group represented by the formula:

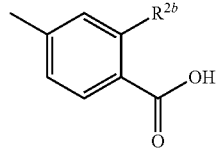

and $R^{2b}$ represents a hydrogen atom or a hydroxy group, or a pharmaceutically acceptable salt thereof.

4. The compound as claimed in claim 2, wherein $R^{1a}$, $R^{1b}$ and $R^{1c}$ independently represent any one of the following (b1) to (b4):

(b1) a hydrogen atom;

(b2) a halogen atom;

(b3) a hydroxy group;

(b4) $C_{1-6}$ alkyl, $C_{1-6}$ alkoxy, mono(di) $C_{1-6}$ alkylamino or hydroxy$C_{1-6}$ alkyl each of which may be substituted by a fluorine atom, or a pharmaceutically acceptable salt thereof.

5. The compound as claimed in claim 1, represented by the formula (II):

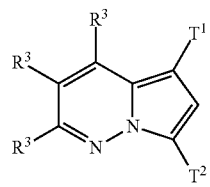
(II)

wherein
one of $T^1$ and $T^2$ represents cyano and the other represents a group represented by the formula:

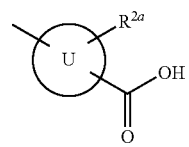

$R^3$ independently represents any one of the following (c1) to (c4):
(c1) a hydrogen atom;
(c2) a halogen atom;
(c3) a hydroxy group;
(c4) $C_{1-6}$ alkyl, $C_{1-6}$ alkoxy, mono(di)$C_{1-6}$ alkylamino, $C_{2-7}$ acyl, $C_{3-8}$ cycloalkyl, 3 to 8-membered heterocycloalkyl, $C_6$ aryl or 5 or 6-membered heteroaryl each of which may have any group selected from substituent group G;
$R^{2a}$ represents a hydrogen atom, a fluorine atom, a hydroxy group or amino; and
ring U and substituent group G have the same meanings as defined in claim 1, or a pharmaceutically acceptable salt thereof.

6. The compound as claimed in claim 5, wherein $R^3$ independently represents any one of the following (d1) to (d4):
(d1) a hydrogen atom;
(d2) a halogen atom;
(d3) a hydroxy group;
(d4) $C_{1-6}$ alkyl, $C_{1-6}$ alkoxy, mono(di)$C_{1-6}$ alkylamino or hydroxy$C_{1-6}$ alkyl each of which may be substituted by a fluorine atom, or a pharmaceutically acceptable salt thereof.

7. The compound as claimed in claim 6, represented by the formula (IIa):

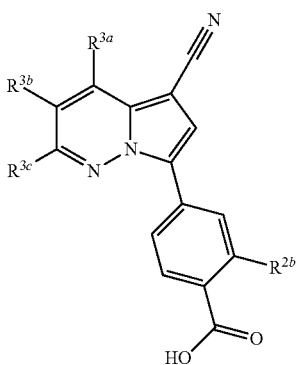
(IIa)

wherein
$R^{2b}$ represents a hydrogen atom or a hydroxy group;
$R^{3a}$, $R^{3b}$ and $R^{3c}$ independently represent any one of the following (e1) to (e4):
(e1) a hydrogen atom;
(e2) a halogen atom;
(e3) a hydroxy group;
(e4) $C_{1-6}$ alkyl, $C_{1-6}$ alkoxy, mono(di)$C_{1-6}$alkylamino or hydroxy$C_{1-6}$ alkyl each of which may be substituted by a fluorine atom, or a pharmaceutically acceptable salt thereof.

8. The compound as claimed in claim 6, represented by the formula (IIb):

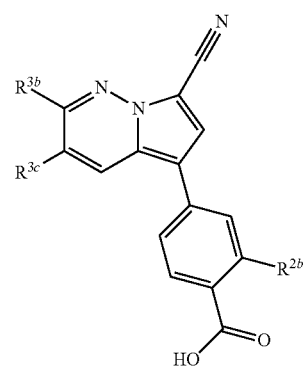
(IIb)

wherein
$R^{2b}$ represents a hydrogen atom or a hydroxy group; and
$R^{3b}$ and $R^{3c}$ independently represent any one of the following (f1) to (f4):
(f1) a hydrogen atom;
(f2) a halogen atom;
(f3) a hydroxy group;
(f4) $C_{1-6}$ alkyl, $C_{1-6}$ alkoxy, mono(di)$C_{1-6}$ alkylamino or hydroxy$C_{1-6}$ alkyl each of which may be substituted by a fluorine atom, or a pharmaceutically acceptable salt thereof.

9. The compound as claimed in claim 7, wherein
$R^{2b}$ is a hydroxy group;
$R^{3a}$ is a hydrogen atom, a fluorine atom or a chlorine atom;
$R^{3b}$ is a hydrogen atom, a fluorine atom, methyl, ethyl or methoxy; and
$R^{3c}$ is a hydrogen atom, a fluorine atom, a chlorine atom, methyl or trifluoromethyl, or a pharmaceutically acceptable salt thereof.

10. The compound as claimed in claim 8, wherein
$R^{2b}$ is a hydroxy group;
$R^{3b}$ is a hydrogen atom, a fluorine atom, methyl, ethyl or methoxy; and
$R^{3c}$ is a hydrogen atom, a fluorine atom, a chlorine atom, methyl or trifluoromethyl, or a pharmaceutically acceptable salt thereof.

11. The compound as claimed in claim 4, represented by the formula (Ij):

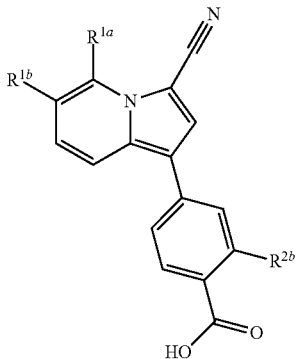

wherein
$R^{2b}$ represents a hydrogen atom or a hydroxy group; and
$R^{1a}$ and $R^{1b}$ have the same meanings as defined in claim 4, or a pharmaceutically acceptable salt thereof.

12. The compound as claimed in claim 11, wherein $R^{2b}$ is a hydroxy group;
$R^{1a}$ is a hydrogen atom, a fluorine atom, a chlorine atom or methyl; and
$R^{1b}$ is a hydrogen atom, a fluorine atom, methyl, ethyl or methoxy, or a pharmaceutically acceptable salt thereof.

13. 4-(7-Cyanopyrrolo[1,2-b]pyridazine-5-yl)-2-hydroxy benzoic acid, or a pharmaceutically acceptable salt thereof.

14. 4(7-Cyano-2-methyl-pyrrolo[1,2-b]pyridazin-5-yl)-2-hydroxy-benzoic acid, or a pharmaceutically acceptable salt thereof.

15. 4-(3Cyano-indolizin-1-yl)-2hydroxyl-benzoie acid, or a pharmaceutically acceptable salt thereof.

16. 4-(5-Cyano-pyrrolo[1,2-b]pyridazin-7-ul)-2-hydroxy-benzoic acid, or a pharmaceutically acceptable salt thereof.

17. A xanthine oxidase inhibitor comprising a compound as claimed in claim 1, or a pharmaceutically acceptable salt thereof as an active ingredient.

18. A pharmaceutical composition comprising a compound as claimed in claim 1, or a pharmaceutically acceptable salt thereof as an active ingredient.

19. A method of treatment of a diease selected from the group consisting of hyperuricemia, gouty tophus, gouty arthritis, tenal disorder associeated with hyperuricemia and Urinary calculi comprising administering an effective amount of the pharmaceutical composition as Claimed in claim 18 to a patient in need thereof.

20. The method of treatment of claim 19, wherein the disease is hyperuricemia.

21. A method for lowering serum uric acid level comprising administering an effective amount of the pharmaceutical composition as claimed in claim 18 to a patient in need thereof.

22. A method of inhibiting the production of uric acid comprising administering an effective amount of the pharmaceutical composition as claimed in claim 18 to a patient in need thereof.

* * * * *